United States Patent
Doguchi et al.

(10) Patent No.: US 7,258,663 B2
(45) Date of Patent: *Aug. 21, 2007

(54) ENDOSCOPE SYSTEM WITH IRRADIATED LIGHT SWITCHING FEATURE

(75) Inventors: Nobuyuki Doguchi, Hino (JP); Yasuo Komatsu, Hachioji (JP); Kazunari Nakamura, Zama (JP); Sakae Takehana, Sagamihara (JP); Katsuichi Imaizumi, Hino (JP); Takayuki Hanawa, Hachioji (JP)

(73) Assignee: Olympus Corporation, Tokyo (JP)

(*) Notice: Subject to any disclaimer, the term of this patent is extended or adjusted under 35 U.S.C. 154(b) by 434 days.

This patent is subject to a terminal disclaimer.

(21) Appl. No.: 10/755,559

(22) Filed: Jan. 12, 2004

(65) Prior Publication Data

US 2004/0143157 A1 Jul. 22, 2004

Related U.S. Application Data

(63) Continuation of application No. 09/743,994, filed on Jan. 17, 2001, now Pat. No. 6,902,527.

(51) Int. Cl.
*A61B 1/045* (2006.01)
*A61B 1/06* (2006.01)

(52) U.S. Cl. .................... 600/109; 600/178; 600/160; 348/65; 348/76

(58) Field of Classification Search ............... 600/109, 600/110, 114, 160, 180, 181, 178, 476; 348/68–72
See application file for complete search history.

(56) References Cited

U.S. PATENT DOCUMENTS

| | | | |
|---|---|---|---|
| 4,667,229 A | 5/1987 | Cooper et al. | |
| 4,821,117 A | 4/1989 | Sekiguchi | |
| 4,951,135 A | 8/1990 | Sasagawa et al. | |
| 4,983,019 A | 1/1991 | Ikuno et al. | |
| 5,337,340 A | 8/1994 | Hynecek | |
| 5,408,263 A | 4/1995 | Kikuchi et al. | |
| 5,475,420 A | 12/1995 | Buchin | |
| 5,589,874 A | 12/1996 | Buchin | |
| 5,749,830 A | 5/1998 | Kaneko et al. | |
| 5,827,190 A | 10/1998 | Palcic et al. | |

(Continued)

FOREIGN PATENT DOCUMENTS

DE 195 35 114 A1 3/1996

(Continued)

*Primary Examiner*—John P. Leubecker
(74) *Attorney, Agent, or Firm*—Scully, Scott, Murphy & Presser, P.C.

(57) ABSTRACT

An endoscope 2 has a CCD 9 incorporated in the distal part of an insertion unit 6 thereof. The sensitivity of the CCD 9 can be varied by applying a plurality of pulsating driving signals so as to change an electron multiplication rate. The endoscope 2 is connected to a processor 3 so that it can be disconnected freely. Information representing a type of endoscope stored in advance in a ROM 48 is transmitted to a controller 21 incorporated in the processor 3. The control means 21 uses a CCD sensitivity control means 12 to control the sensitivity of the CCD 9 according to the type of connected endoscope 2. Consequently, a view image of proper brightness can be produced irrespective of the type of endoscope 2.

22 Claims, 29 Drawing Sheets

U.S. PATENT DOCUMENTS

| | | |
|---|---|---|
| 6,099,466 A | 8/2000 | Sano et al. |
| 6,217,510 B1 | 4/2001 | Ozawa et al. |
| 6,293,911 B1 | 9/2001 | Imaizumi et al. |
| 6,462,770 B1 | 10/2002 | Cline et al. |

FOREIGN PATENT DOCUMENTS

| | | |
|---|---|---|
| DE | 196 19 734 A1 | 11/1996 |
| JP | 61-48333 | 3/1986 |
| JP | 1-155292 | 6/1989 |
| JP | 1-217415 | 8/1989 |
| JP | 1-221135 | 9/1989 |
| JP | 1-297043 | 11/1989 |
| JP | 5-252450 | 9/1993 |
| JP | 5-253180 | 10/1993 |
| JP | 6-125871 | 5/1994 |
| JP | 6-222287 | 8/1994 |
| JP | 7-23278 | 1/1995 |
| JP | 8-111812 | 4/1996 |
| JP | 8-280692 | 10/1996 |
| JP | 8-313826 | 11/1996 |
| JP | 9-24023 | 1/1997 |
| JP | 9-55878 | 2/1997 |
| JP | 9-70384 | 3/1997 |
| JP | 9-80319 | 3/1997 |
| JP | 10-151104 | 6/1998 |
| JP | 11-113839 | 4/1999 |
| JP | 11-122540 | 4/1999 |

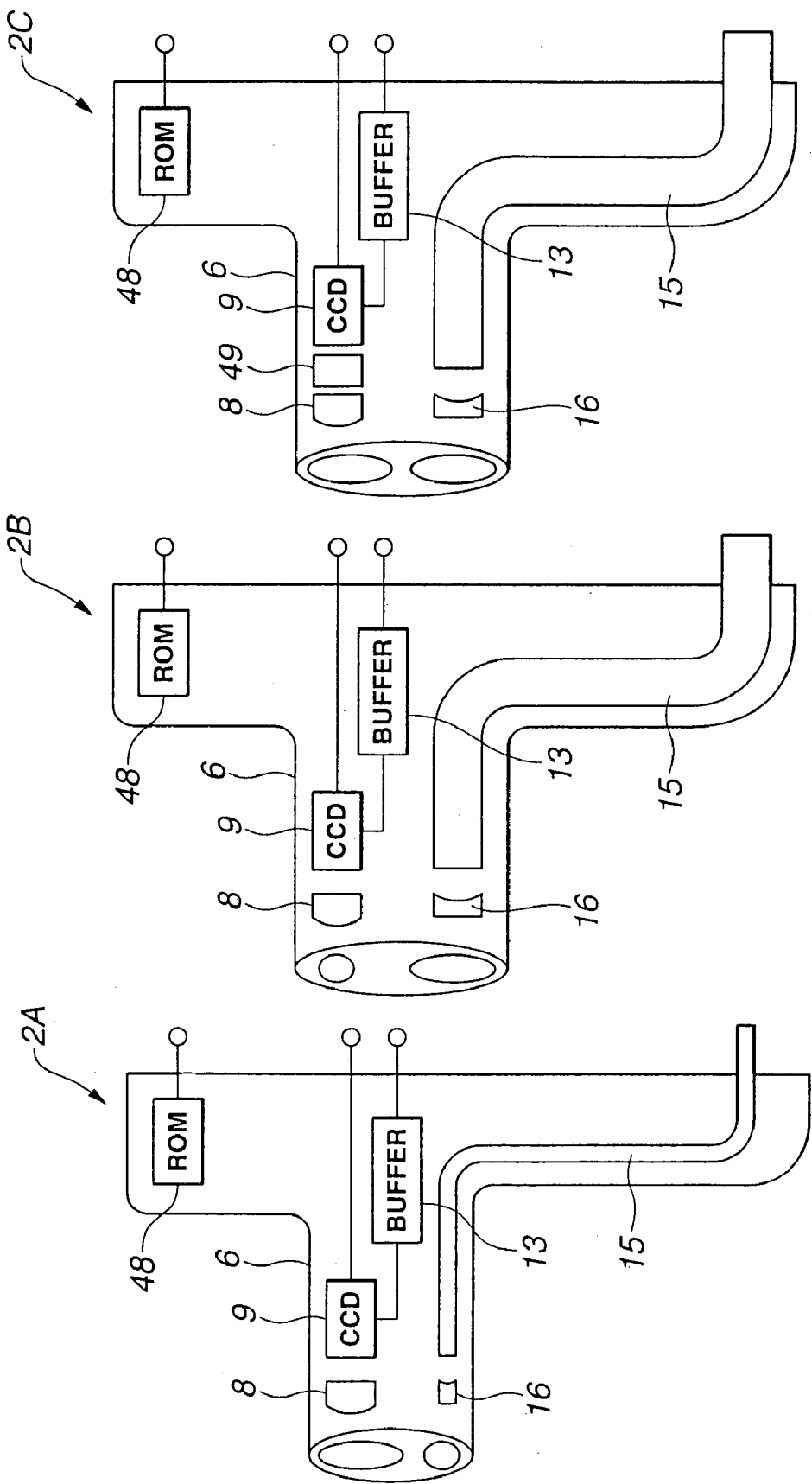

FIG.5

| | PURPOSE OF USE | NUMBER OF OPTICAL FIBERS CONSTITUTING LIGHT GUIDE | F-NUMBER | NUMBER OF APPLICATIONS OF PULSE φCMD (REQUIRED SENSITIVITY) |
|---|---|---|---|---|
| ENDOSCOPE 2 | OBSERVATION UNDER ORDINARY LIGHT (LARGE DIAMETER) | 6000 - | f = 5.6 | 0 (×1.0) |
| ENDOSCOPE 2A | OBSERVATION UNDER ORDINARY LIGHT (SMALL DIAMETER) | 3000 - | f = 5.6 | 70 (×2.0) |
| ENDOSCOPE 2B | OBSERVATION UNDER ORDINARY LIGHT (LARGE DEPTH OF FIELD) | 6000 - | f = 8.0 | 70 (×2.0) |
| ENDOSCOPE 2C | OBSERVATION UNDER SPECIAL LIGHT (OBSERVATION UNDER LIGHT STEMMING FROM FLUORESCENCE) | 6000 - | f = 5.6 | 392 (×50) |

ORDINARY SENSITIVITY

MULTIPLICATION OF ELECTRONS

ENDOSCOPE SYSTEM WITH IRRADIATED LIGHT SWITCHING FEATURE

RELATED APPLICATIONS

This application is a continuation application of U.S. application Ser. No. 09/743,994, filed Jan. 17, 2001, now U.S. Pat. No. 6,902,527.

TECHNICAL FIELD

The present invention relates to an endoscope system for visualizing an object using a solid-state imaging device whose sensitivity is controllable.

BACKGROUND ART

An endoscope system having a solid-state imaging device consists mainly of an endoscope such as an electronic endoscope, a processor, a light source unit, and a monitor. In the endoscope system, the insertion unit of the endoscope is inserted into a body cavity, and illumination light emanating from the light source unit is irradiated to an object over a light guide lying through the endoscope. The solid-state imaging device incorporated in the distal part of the endoscope photoelectrically converts the light to produce a video signal. The processor processes the signal and displays an image on the monitor according to the signal.

Talking of the endoscope system, a field-sequential endoscope system like the one disclosed in, for example, Japanese Unexamined Patent Application Publication No. 1-221135 is known as a modality enabling observation under ordinary light by utilizing illumination light of wavelengths falling within the visible spectrum. In the endoscope system, as described in Japanese Unexamined Patent Application Publication No. 9-70384, an endoscope designed for fluorescence diagnosis is often employed in order to discover an early-stage carcinoma or the like. Specifically, excitation light is irradiated to a living tissue, and light stemming from fluorescence exhibited by the living tissue is observed in order to discover an early-stage carcinoma or the like.

An imaging device included in such a fluorescence diagnosis endoscope system is requested to offer so high sensitivity as to enable observation of feeble light stemming from fluorescence. For this reason, a pickup tube is often employed. Japanese Unexamined Patent Application Publication No. 5-252450 has disclosed a technology of controlling a drain voltage occurring due to overflow in a solid-state imaging device according to an output signal of the solid-state imaging device. The technology thus enables visualization of a region whose image cannot be corrected by controlling an amount of light using an iris diaphragm.

Problems to be Solved by the Invention

In the foregoing endoscope system, various types of endoscopes are switched for use according to a region to be assessed or a method of assessment. For example, an endoscope dedicated to examination of the bronchi is thinner than an endoscope dedicated to examination of the large intestine.

The diameter of an endoscope affects the number of optical fibers constituting a light guide lying through the endoscope, and brings about a difference in the amount of irradiated light. Moreover, an f-number varies depending on the purpose of use of an endoscope. In particular, when an endoscope having a large f-number set therefore is used to observe an object located at a far point, the amount of light is so small that a view image is dark.

This causes a range, within which a proper amount of light necessary for picking up image data is collected, to greatly vary depending on a type of endoscope. On the other hand, as mentioned above, the endoscope system is usable not only for observation under ordinary light but also for observation under special light such as light stemming from fluorescence intended to assess a lesion. For the observation under light stemming from fluorescence, very feeble light stemming from auto-fluorescence must be collected. Therefore, a solid-state imaging device to be incorporated in the distal part of an endoscope is requested to offer much higher sensitivity than a solid-state imaging device designed for observation under ordinary light.

In general, when the endoscope system is used to observe an object that makes quick motion or to produce a still image, the solid-state imaging device is driven using an electronic shutter. In this case, the amount of irradiated light is increased in order to optimize an exposure value. However, when an iris diaphragm is fully opened in order to adjust the amount of irradiated light, if the electronic shutter is activated, the exposure value becomes insufficient. This results in a dark image. Automatic gain control (AGC) may be utilized to compensate the insufficient exposure value. However, this poses a problem in that a noise is intensified.

An object of the present invention is to provide an endoscope system capable of producing a view image of proper brightness irrespective of a type of endoscope. Specifically, the sensitivity of a solid-state imaging device is controlled depending on the type of endoscope, that is, the diameter of an insertion unit of an endoscope, an f-number set for an endoscope, or whether an endoscope is designed for observation under ordinary light or observation under special light such as light stemming from fluorescence.

Another object of the present invention is to provide an endoscope system capable of offering a proper exposure value by controlling the sensitivity of a solid-state imaging device according to movement information concerning the light source, whether an amount of light supplied from a light source is insufficient or not.

Still another object of the present invention is to provide an endoscope system capable of producing a view image less affected by a noise by controlling the sensitivity of a solid-state imaging device according to the driven state of the solid-state imaging device.

DISCLOSURE OF INVENTION

The present invention has paid attention to a technology of multiplying charge through ionization to improve sensitivity as described in the U.S. Pat. No. 5,337,340 entitled "Charge Multiplying Detector (CMD) Suitable for Small Pixel CCD Image Sensors." According to the technology, an electric field of sufficient strength is produced, and conduction electrons are collided against atoms in the electric field. The electrons are thus released from a valence band, and escaped from an area in which the conduction electrons collide against the atoms. Owing to the ionization, charge carriers are multiplied.

According to the present invention, there is provided an endoscope system consisting mainly of an endoscope, a signal processing unit, a light source unit, and a sensitivity control means. The endoscope has a solid-state imaging device whose sensitivity can be varied by applying a plurality of different driving pulses to change an electron multiplication rate. The signal processing unit processes a signal output from the solid-state imaging device. The light source unit irradiates light to an object so that an object image will be projected on the solid-state imaging device. The sensitivity control means varies a sensitivity control pulse, applies it to the solid-state imaging device, and thus controls the electron multiplication rate for the solid-state imaging device.

According to the present invention, there is provided an endoscope system consisting mainly of an endoscope, a signal processing unit, a light source unit, a switching means, and a sensitivity control means. The endoscope has a solid-state imaging device whose sensitivity can be varied by applying a plurality of different pulsating driving signals to change an electron multiplication rate. The signal processing unit processes a signal output from the solid-state imaging device. The light source unit irradiates white light or special light of a specified wavelength band to an object with the intensity of light varied. The switching means switches observation in an ordinary light mode in which the white light is irradiated and observation in a special light mode. The sensitivity control means varies a sensitivity control pulse, applies it to the solid-state imaging device, and controls an electron multiplication rate for the solid-state imaging device.

According to the present invention, the sensitivity control means included in the endoscope system is controlled based on at least one of a designating signal output from a designating means, an information signal output from a connected endoscope and representing a feature of the endoscope, a movement information signal output from the light source unit, a signal representing a driving condition for the solid-state imaging device, and an output signal of the signal processing unit.

In the endoscope system according to the present invention, the sensitivity can be controlled freely by adjusting an amplitude of a sensitivity control pulse (CMDgate pulse) or the number of applications of the sensitivity control pulse per unit time. Since the sensitivity can be controlled, a high-sensitivity solid-state imaging device can be realized without a noise derived from multiplication and without the necessity of cooling. This results in an endoscope capable of offering high image quality and being inserted smoothly.

In the endoscope system according to the present invention, the sensitivity control means is included in the signal processing unit. The sensitivity of the solid-state imaging device is determined based on a type of endoscope or a property of each solid-state imaging device. Consequently, a view image of proper brightness can be produced irrespective of the type of endoscope or the property of each solid-state imaging device.

BRIEF DESCRIPTION OF THE DRAWINGS

FIG. 1 to FIG. 6 are concerned with Example 1 of the present invention;

FIG. 1 is a block diagram showing the overall configuration of an endoscope system;

FIG. 2 is a block diagram showing the configuration of a signal pre-processing means included in a signal processing means;

FIG. 3 is a block diagram showing the configurations of a field-sequential signal synchronizing means and a signal post-processing means which are included in the signal processing means;

FIG. 4 is an explanatory diagram showing various types of endoscopes employed in the present example;

FIG. 5 is an explanatory diagram concerning the purposes of use of the endoscopes;

FIG. 6 is an explanatory diagram concerning actions;

FIG. 13 is a block diagram showing the overall configuration of an endoscope system;

FIG. 14 is a block diagram showing in detail the configuration of a signal pre-processing means;

FIG. 15 shows in detail the structure of a CCD;

FIG. 16 is an explanatory diagram indicating an action performed with ordinary sensitivity and an action performed with electrons multiplied;

FIG. 17 is a block diagram schematically showing the configuration of an endoscope system;

FIG. 18 is an explanatory diagram showing the arrangement of two filter sets constituting a rotary filter;

FIG. 19 is a block diagram showing a signal pre-processing signal included in a signal processing means;

FIG. 20 is a block diagram showing a field-sequential synchronizing means and a signal post-processing means which are included in the signal processing means;

FIG. 21 is a timing chart indicating the timings of signals used to drive a CCD;

FIG. 22 is a graph indicating the relationship between the illuminance on the imaging surface of a CCD and a signal-to-noise ratio;

FIG. 23 is a graph indicating the relationship between the illuminance on the imaging surface of the CCD and an output voltage level;

FIG. 24 shows the structure of a rotary filter;

FIG. 25 is a timing chart indicating the timings of signals used to drive a CCD in a special light mode;

FIG. 26 is a graph indicating the relationship between the illuminance on the imaging surface of the CCD and a signal-to-noise ratio (long exposure);

FIG. 27 is a graph indicating the relationship between the illuminance on the imaging surface of the CCD and an output voltage level (long exposure);

FIG. 28 is a block diagram schematically showing an endoscope system;

FIG. 29 is a block diagram schematically showing a signal pre-processing means included in a signal processing means.

BEST MODE FOR CARRYING OUT THE INVENTION

Examples of the present invention will be described with reference to the drawings below.

EXAMPLE 1

Figure 1:
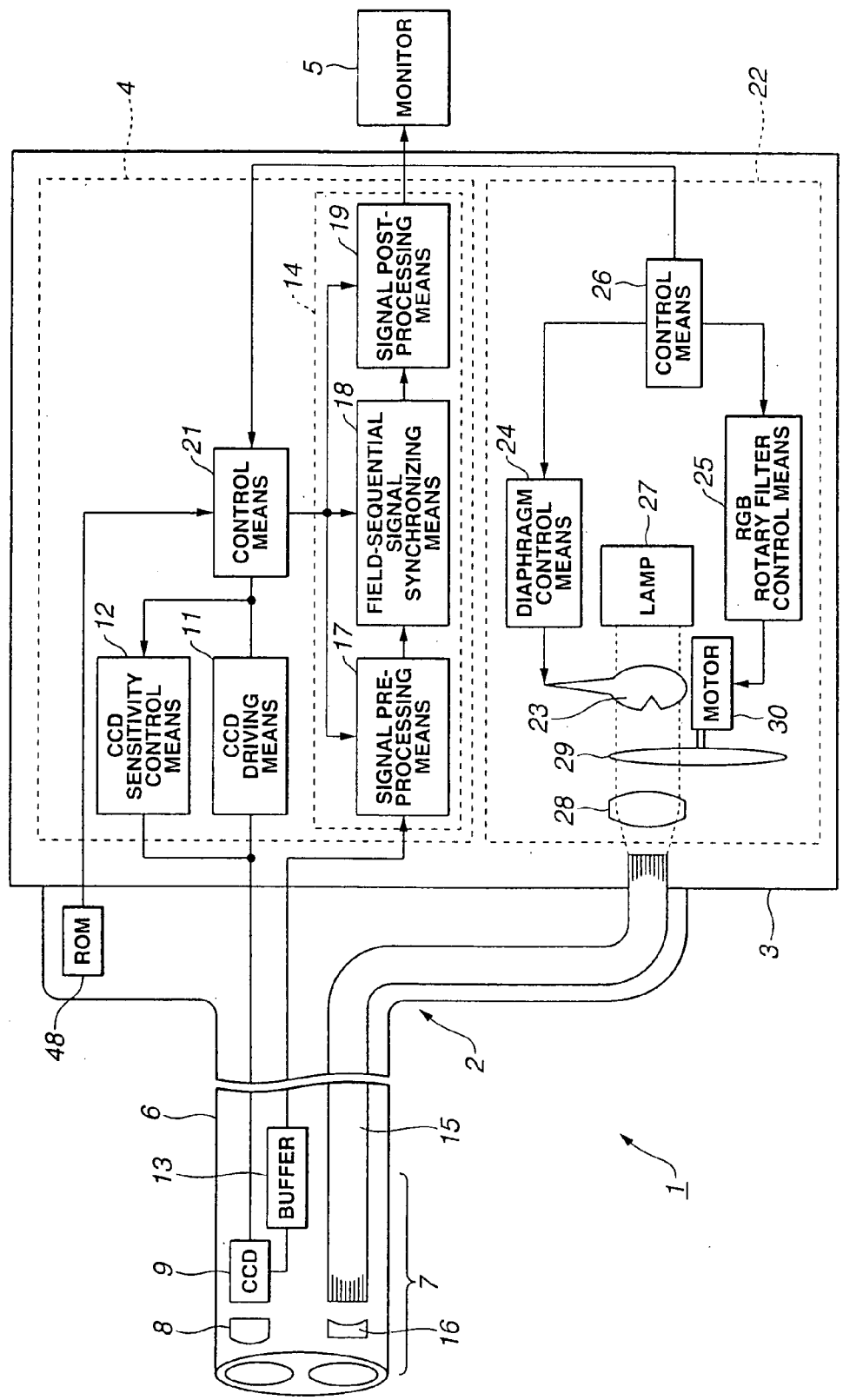
Figure 2:
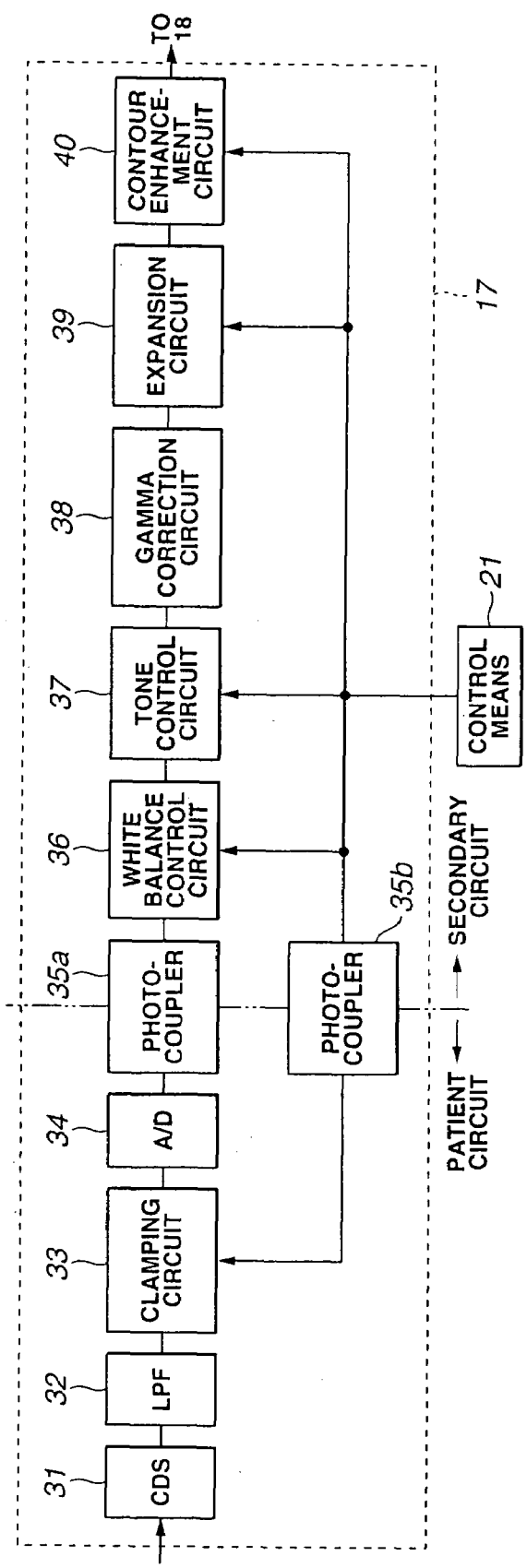
Figure 3:
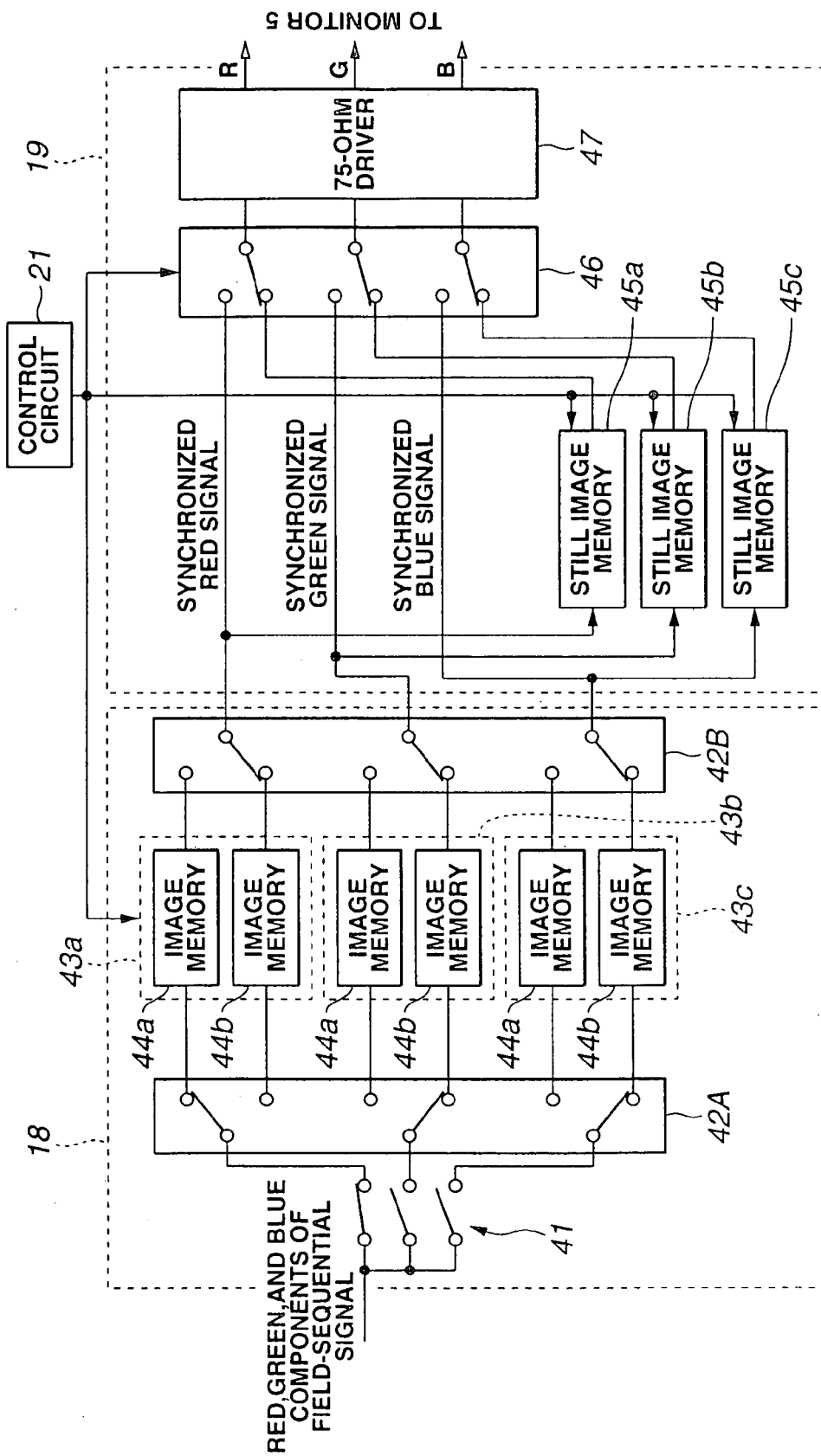
Figure 6:
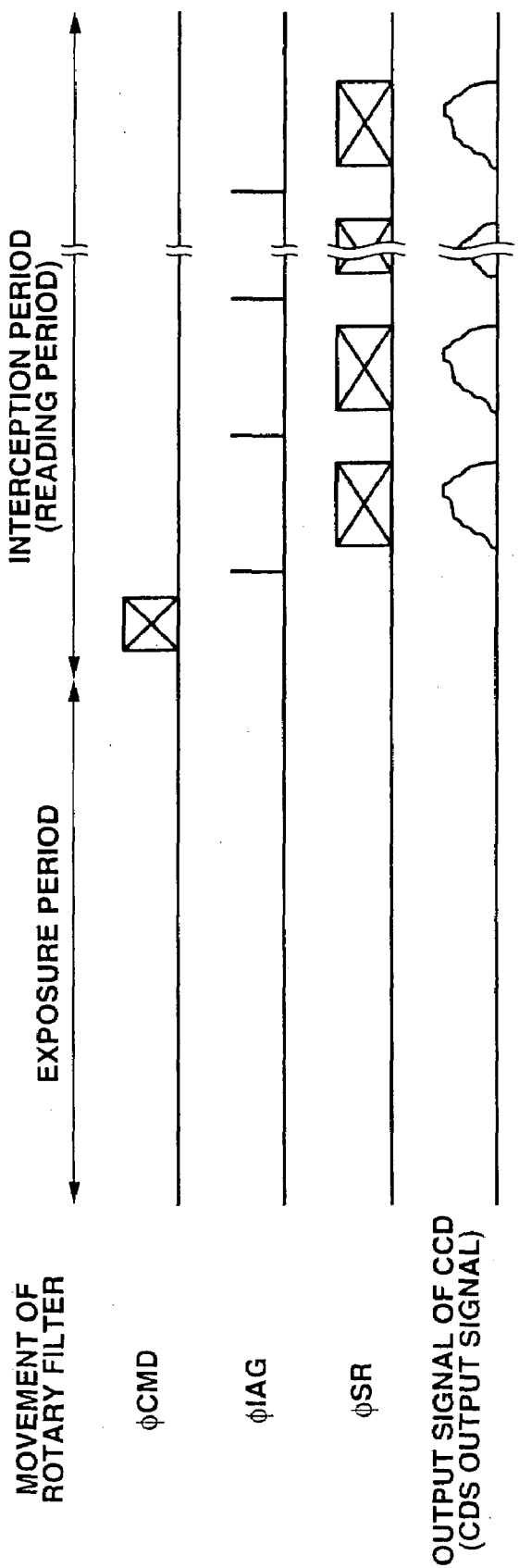

FIG. 1 to FIG. 6 are concerned with Example 1 of the present invention. FIG. 1 is a block diagram schematically showing the configuration of an endoscope system of Example 1. FIG. 2 and FIG. 3 show a signal pre-processing means included in a signal processing means. FIG. 4 shows various types of endoscopes employed in the present example. FIG. 5 describes the purposes of use of the endoscopes and others. FIG. 6 is an explanatory diagram concerning actions.

As shown in FIG. 1, an endoscope system 1 of Example 1 of the present invention consists mainly of an electronic endoscope (hereinafter, for brevity's sake, an endoscope) 2, a processor 3, and a monitor 5. A solid-state imaging device is incorporated in the endoscope 2. The endoscope 2 is connected to the processor 3 so that it can be disconnected freely, and a signal processing unit 4 and a field-sequential light source unit 22 are incorporated in the processor 3. The monitor 5 is connected to the processor 3, and a video signal processed by the processor 3 is output to the monitor 5.

The endoscope 2 has an elongated insertion unit 6 that is inserted into a body cavity. An objective 8 through which an object image is projected is incorporated in the distal part 7 of the insertion unit 6. A solid-state imaging device, for example, a charge-coupled device (hereinafter a CCD) is located on the image plane of the objective 8. The CCD 9 is connected to a CCD driving means 11 and a CCD sensitivity control means 12, which are included in the signal processing unit 4 incorporated in the processor 3, over a signal line. Exposure and reading are controlled based in a driving signal and a sensitivity control signal produced by the CCD driving means 11 and CCD sensitivity control means 12 respectively.

In the CCD 9, as described in the U.S. Pat. No. 5,337,340 entitled "Charge Multiplying Detector (CMD) suitable for Small Pixel CCD Image Sensors," an electric field of sufficient strength is produced, and conduction electrons are collided against atoms in the electric field. The electrons are released from a valence band and escaped from an area in which the conduction electrons collide against the atoms. Owing to the ionization, charge carriers are multiplied, and the sensitivity of the CCD is improved. Moreover, the sensitivity of the CCD is freely controllable by adjusting an amplitude of an external control pulse (CMDgate pulse) and the number of applications of the control pulse per unit time.

Consequently, a high-sensitivity CCD is realized without a noise derived from multiplication performed for improving sensitivity and without the necessity of cooling. The CCD is therefore ideal for realization of an endoscope offering excellent image quality and being inserted smoothly. The CCD 9 is connected to a signal processing means 14 included in the processor 3 via a buffer 13. An object image projected on the imaging surface of the CCD 9 through the objective 8 is converted into an electric signal by the CCD 9, and read from the CCD 9. The output of the CCD 9 is then fed to the signal processing means 14.

A light guide 15 over which illumination light is propagated lies through the endoscope 2. An illumination lens 16 is located in front of the distal end of the light guide 15. Illumination light-propagated through the endoscope 2 over the light guide 15 is irradiated to an object through the illumination lens 16.

The signal processing means 14 consists of a signal pre-processing means 17, a field-sequential signal synchronizing means 18, and a signal post-processing means 19. The signal pre-processing means 17 performs various kinds of signal processing on an output signal of the CCD 9. The field-sequential signal synchronizing means 18 synchronizes field-sequential signal components output from the signal pre-processing means 17. The signal post-processing means 19 performs various kinds of signal processing on an output signal of the field sequential signal synchronizing means 18 so that the output signal can be output to the monitor 5. An output signal read from the CCD 9 is converted into a television signal, and the television signal is output to the monitor 5.

The CCD driving means 11, CCD sensitivity control means 12, and signal processing means 14 are connected to a (first) control means 21. The control means 21 extends control.

The control means 21 is connected to a (second) control means 26 for controlling an iris diaphragm 23, a diaphragm control means 24, and an RGB rotary filter control means 25 which are included in the field-sequential light source unit 22 for supplying field-sequential illumination light rays to the endoscope 2. Interlocked with the RGB rotary filter, control means 25, the control means 21 controls the CCD driving means 11 and signal processing means 14.

Moreover, the field-sequential light source unit 22 includes a lamp 27, a condenser lens 28, and a RGB rotary filter 29. The lamp 27 generates illumination light. The condenser lens 28 converges the illumination light on the rear end of the light guide 15. The RGB rotary filter 29 is interposed between the lamp 27 and condenser lens 28.

The rotary filter 29 is coupled to the rotation shaft of a motor 30 so that it can rotate. The rotary filter 29 is controlled by the RGB rotary filter control means under control of the control means 26 so that it will rotate at a predetermined rotating speed. Consequently, red, green, and blue field-sequential light rays are supplied to the rear end of the light guide 15.

The signal processing means 14 has the signal pre-processing means 17 thereof configured as shown in, for example, FIG. 2. Field-sequential signal components output from the endoscope are input to the signal pre-processing means 17.

In the signal pre-processing means 17, the output signal of the CCD 9 passes through a CDS circuit 31, a low-pass filter (LPF) 32, and a clamping circuit 33, and is then digitized by an A/D converter 34. The resultant digital signal is isolated from a patient circuit and transmitted to a secondary circuit by a photocoupler 35a.

The secondary circuit includes a white balance control circuit 36, a tone control circuit 37, and a gamma correction circuit 38. After subjected to white balance control, tone control, and gamma correction are carried out, an expansion circuit 39 performs electronic zooming to achieve expansion. An output signal of the expansion circuit 39 is input to the field sequential signal synchronizing means 18 via a contour enhancement circuit 40.

The control means 21 outputs a control signal used to control the white balance control circuit 36, tone control circuit 37, expansion circuit 39, and contour enhancement circuit 40 which are included in the secondary circuit. Moreover, the control means 21 outputs a control signal, which is used to control the clamping circuit 33 included in the patient circuit, via a photocoupler 35b serving as an isolating/transmitting means.

Red, green, and blue field-sequential signal components output from the signal pre-processing means 17 are input to synchronizing means 43a, 43b, and 43c via selector switches 41, 42A, and 42B included in the field-sequential signal synchronizing means 18 shown in FIG. 3.

The synchronizing means 43a, 43b, and 43c each have a memory in which data for at least one field can be stored. The red, green, and blue field-sequential signal components that are input in that order are stored in the memories associated with the respective colors. The stored field-sequential signal components are read simultaneously and output as synchronous signal components.

As an example of the synchronizing means 43a, 43b, and 43c, each synchronizing means 43i (where i denotes a, b, or c) shown in FIG. 3 consists of image memories 44a and 44b in each of which data for at least two fields can be stored. Herein, writing and reading of an image signal in and from the image memories 44a and 44b are alternately switched for the purpose of synchronization.

Synchronous signal components output from the synchronizing means 43a, 43b, and 43c are input to still image memories 45a, 45b, and 45c, in each of which a still image signal component is stored, included in the signal post-processing means 19, and also input to a selector 46.

The synchronous signal components output from the synchronizing means 43a, 43b, and 43c are fed as motion picture signal components to the monitor 5 via the selector 46 and a 75-ohm driver 47 installed as a succeeding stage of the selector 46. The output terminals of the still image memories 45a, 45b, and 45c are connected to the other input terminals of the selector 36.

The control means 21 controls writing and reading of an image signal component in and from the still image memories 45a, 45b, and 45c. In response to an external Freeze instruction, the control means 21 controls the still image memories 45a, 45b, and 45c so that image signal components to be frozen will be stored therein. The control means 21 controls the selector 46 so that the selector 46 will select still image signal components and feed them to the monitor 5 via the 75-ohm driver 47 on the succeeding stage. Herein, the selector 46 selects either of the motion picture signal components output from the synchronizing means 43a, 43b, and 43c and the still image signal components output from the still image memories 45a, 45b, and 45c.

A ROM 48 in which information inherent to the endoscope 2 is stored is incorporated in the endoscope 2. At the time when the endoscope 2 is connected to the processor 3, the information is transmitted to the control means 21 included in the signal processing unit 4 incorporated in the processor 3. The sensitivity of the CCD 9 is then controlled. In short, the ROM 48 serves as a designating means for designating the sensitivity of the CCD 9.

As shown in FIG. 4, aside from the endoscope 2, various types of endoscopes 2I (where I denotes A, B, or C) are available for different regions to be observed or different purposes of use. Specifically, the endoscope 2A has a smaller number of optical fibers constituting the light guide 15 than the endoscope 2 to thus have a smaller diameter. The endoscope 2B offers a larger f-number than the endoscope 2 to thus offer a larger depth of field. The endoscope 2C has a filter 49, which transmits only light stemming from fluorescence exhibited by a living body for the purpose of observation under light stemming from fluorescence, disposed in front of the CCD 9. The various types of endoscopes 2I can be connected to the processor 3 so that they can be disconnected freely.

FIG. 5 lists the features of the endoscopes 2 and 2I. Information of the features (for example, information representing the number of applications of a sensitivity control pulse φCMD per unit time) is stored in advance in the ROM 48. The information read from the ROM 48 incorporated in the endoscope 2 or 2I connected to the processor 3 is sent to the control means 21. The control means 21 determines the sensitivity of the CCD 9 serving as a solid-state imaging device so that the endoscope 2, 2A, or 2B designed for observation under ordinary light can offer a proper exposure value.

Herein, a sensitivity control value with which the sensitivity of the CCD 9 is controlled is calculated on the assumption that the amount of light supplied from the light source unit 22 to the rear end of the light guide 15 remains constant. The sensitivity control value causes the voltage level of an output signal of the CCD 9 to remain intact irrespective of the number of optical fibers constituting the light guide and the f-number set for an endoscope. When the number of optical fibers constituting the light guide and the f-number are different, information representing the different number of optical fibers and a different f-number is supplied.

For example, when the number of optical fibers constituting the light guide is small, control is extended to make the sensitivity of the CCD 9 higher than it is when the number of optical fibers is large.

When the endoscope 2C designed for observation under light stemming from fluorescence is employed, information representing the fact that the endoscope 2C is employed is transmitted in advance. The sensitivity is set to a predetermined value. Based on the set value, the control means 21 controls the CCD driving means 11 and CCD sensitivity control means 12. FIG. 6 shows driving signals and a sensitivity control signal output from the CCD driving means 11 and CCD sensitivity control means 12 respectively.

FIG. 6 indicates an exposure period and an interception period (reading period) determined by the RGB rotary filter. FIG. 6 also indicates the relationship among a sensitivity control pulse φCMD, a vertical transfer pulse φIAG, and a horizontal transfer pulse φSR which are applied to the CCD 9 and an output signal of the CCD.

The sensitivity of the CCD 9 may be controlled by adjusting either the number of applications of the pulse φCMD per unit time or the amplitude thereof. Herein, the number of applications of the pulse φCMD per unit time is adjusted in order to attain desired sensitivity. In this case, the sensitivity control pulse φCMD is applied to the CCD 9 during the interception (reading) period succeeding the exposure period in order to improve the sensitivity of the CCD 9. The vertical transfer pulse φIAG and horizontal transfer pulse φSR are then applied to the CCD 9 in order to acquire an output signal of the CCD 9.

For example, the number of applications of the sensitivity control pulse φCMD per unit time is varied depending on whichever of the endoscopes 2 and 2I is connected for the purpose of use described in FIG. 5. Sensitivity of a level required by any of the endoscopes 2 and 2I is thus attained readily.

Incidentally, for brevity's sake, electrons shall be multiplied by 1% with each application of the pulse φCMD listed in FIG. 5.

In the endoscope 2C designed for observation under light stemming from fluorescence, the filter 49 having a property of passing light which stems from fluorescence exhibited by a living body and of which wavelengths range from 480 nm to 600 nm is disposed in front of the CCD 9. Only feeble light stemming from fluorescence exhibited by a living body excited with a blue field-sequential light ray (whose wavelengths range from 400 nm to 500 nm) is converted into a video signal by the CCD 9 whose sensitivity has been raised.

The synchronizing means 43a, 43b, and 43c included in the processor 3 store signal components derived from the blue light ray alone simultaneously in the memories associated with the three colors. The synchronizing means 43a, 43b, and 43c read the stored field-sequential signal components simultaneously and output them as monochrome image signal components.

The foregoing control is extended by the control means 21. Signal processing intended to enable observation under ordinary light and signal processing intended to enable observation under light stemming from fluorescence are switched based on information read from the ROM 48 incorporated in any of the endoscopes 2, and 2A to 2C.

As mentioned above, according to the present example, the sensitivity of a solid-state imaging device is controlled based on the type of endoscope connected, that is, whichever of the endoscopes 2 and 2I is connected. Consequently, the endoscope system 1 can produce a view image of proper brightness.

Information read from the ROM 48 may represent a parameter such as a light distribution curve or an angle of view or a correction value with which a difference in brightness from one solid-state imaging device to another. Needless to say, a set value of the sensitivity of the CCD 9 may be transmitted to the processor 3.

According to the present example, the sensitivity of the CCD 9 incorporated in the endoscope 2 or 2I is designated based on information stored in the ROM 48 incorporated therein. In case of an endoscope (for example, the endoscope 2D) not having the ROM 48, an input means such as a keyboard (or a sensitivity designating means) may be connected to the control means 21 incorporated in the signal processing unit 4. In this case, the input means is used to enter a value of sensitivity permitting the endoscope 2D to produce a proper view image. The CCD sensitivity control means 12 controls the sensitivity of the CCD 9 incorporated in the endoscope 2D under control of the control means 21.

Instead of entering a value of sensitivity using the input means, a feature of the endoscope 2D, or more particularly, the number of optical fibers constituting the light guide or an f-number listed in FIG. 5 may be entered. The control means 21 then calculates the required number of applications of the sensitivity control pulse φCMD per unit time, and instructs the CCD sensitivity control means 12 to control the sensitivity of the CCD 9.

EXAMPLE 2

Figure 7:
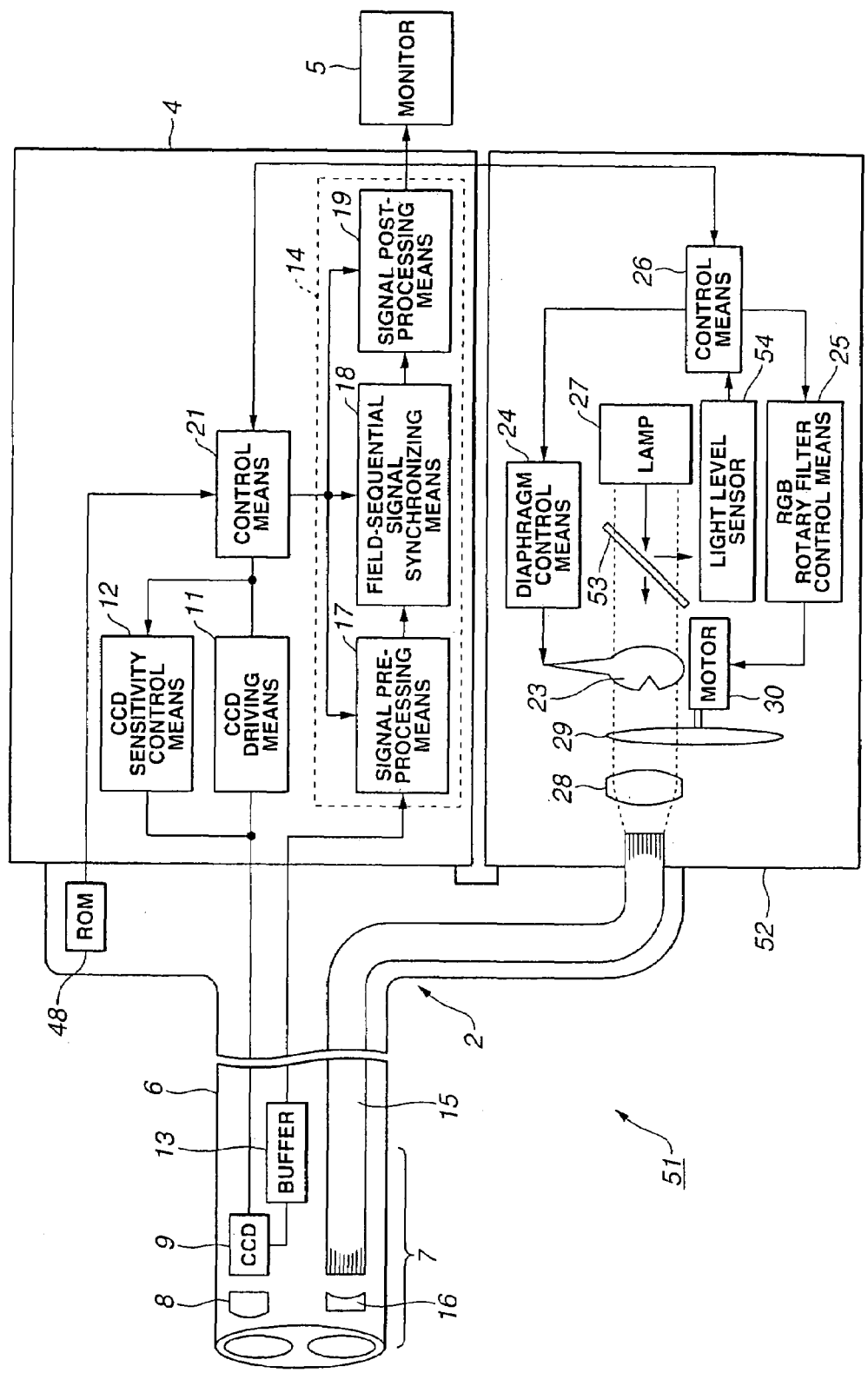
FIG. 7 is a block diagram showing the overall configuration of an endoscope system in accordance with Example 2 of the present invention.

FIG. 7 shows the configuration of an endoscope system 51 in accordance with Example 2 of the present invention. The description of components identical to those shown in FIG. 1 will be omitted.

In Example 1, the field-sequential light source unit 22 is incorporated in the processor 3 together with the signal processing unit 4 including the signal processing means 14. In Example 2, a field-sequential light source unit 52 is included independently of the signal processing unit 4.

In the field-sequential light source unit 52, a half mirror 53 is disposed in front of the lamp 27. The half mirror 53 splits light emitted from the lamp 27. Light reflected from the half mirror 53 is routed to a light level sensor 54.

The amount of light emitted from the lamp 27 decreases with an increase in a lamp lighting time. The light level sensor 54 converts the decrease in the amount of light into numerical data. The numerical data is sent to the control means 21 via the control means 26. The control means 21 calculates a set value of the sensitivity of the CCD 9, which can compensate the decrease in the amount of light emitted from the lamp 27, according to the numerical data, and thus controls the CCD sensitivity control means 12.

The diaphragm control means 24 sends information to the control means 21 via the control means 26. The information represents whether light can be adjusted using the iris diaphragm 23 or whether the iris diaphragm 23 is fully opened or closed.

When the iris diaphragm 23 is fully opened, the control means 21 controls the CCD sensitivity control means 12 so that the CCD sensitivity control means 12 will raise the set value of the sensitivity of the CCD 9. When the iris diaphragm 21 is fully closed, the control means 21 controls the CCD sensitivity control means 12 so that the CCD sensitivity control means 12 will lower the set value of the sensitivity of the CCD 9. The set value of sensitivity may be varied stepwise or continuously. The other components are identical to those of Example 1.

Example 2 exerts the same operations as Example 1. In addition, a means for eliminating the influence of a change in the amount of light emitted actually from the lamp 27 by controlling the sensitivity of the CCD 9 using the CCD sensitivity control means 12 is included in consideration of the time-passing change in the amount of light emitted from the lamp 27.

According to Example 2, even if the amount of light emitted from the lamp 27 incorporated in the light source unit 52 decreases or light cannot be adjusted using the iris diaphragm 23, the endoscope system 51 can produce a view image of proper brightness. This is because the sensitivity of the CCD 9 serving as a solid-state imaging device is controlled based on information sent from the light source unit 52.

EXAMPLE 3

Figure 8:
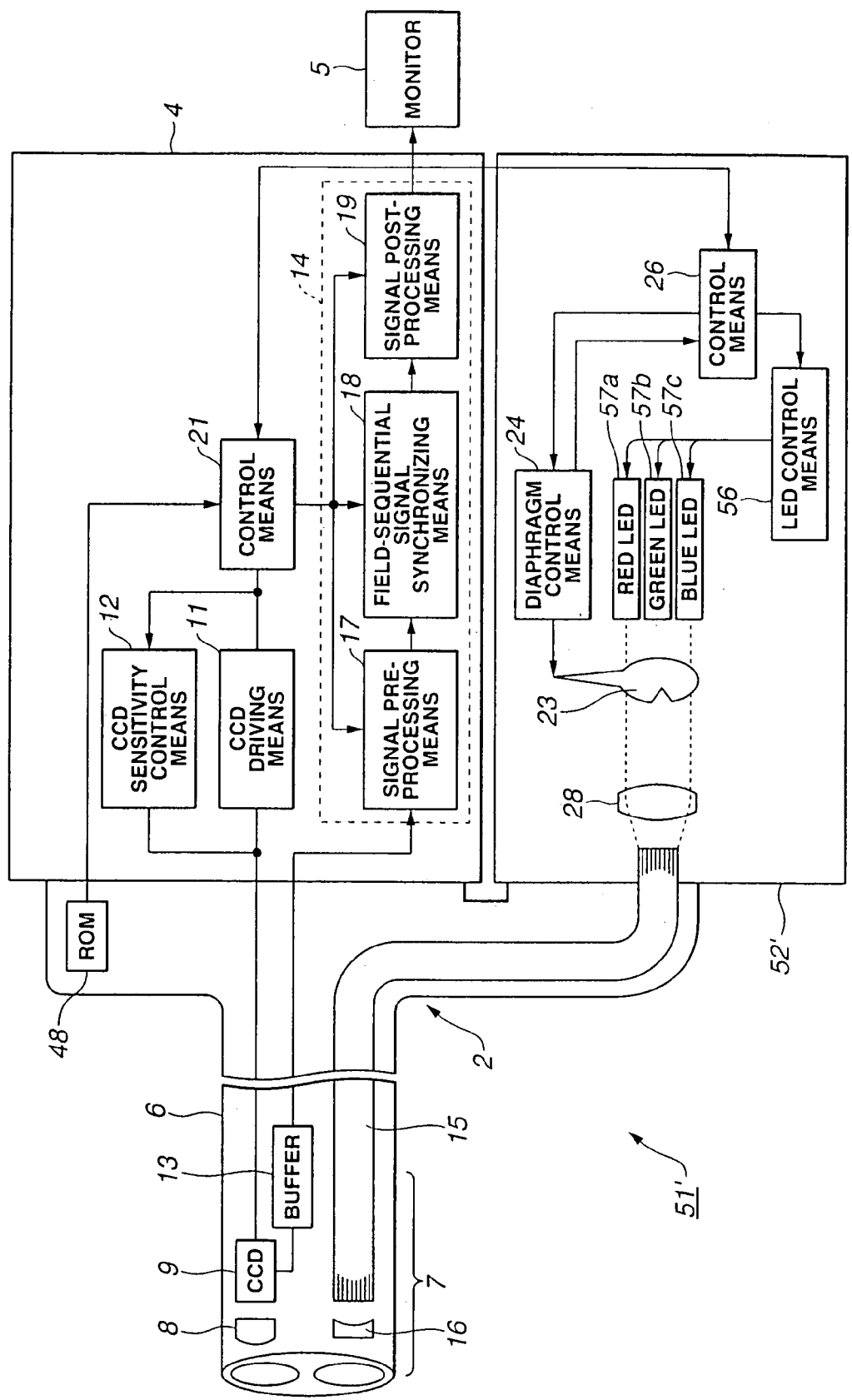
FIG. 8 is a block diagram showing the overall configuration of an endoscope system in accordance with Example 3 of the present invention.

FIG. 8 shows the configuration of an endoscope system 51' in accordance with Example 3 of the present invention. The description of components identical to those shown in FIG. 1 and FIG. 7 will be omitted below. In Example 3, an LED light source unit 52' shown in FIG. 8 may be substituted for the field-sequential light source unit 52 of Example 2 shown in FIG. 7.

The LED light source unit 52' shown in FIG. 8 includes a red LED 57a, a green LED 57b, a blue LED 57c, and a condenser lens 28. The red LED 57a, green LED 57b, and blue LED 57c are connected to an LED control means 56 and lit sequentially. The condenser lens 28 converges the illumination light on the rear end of the light guide 15. Thus, field-sequential light rays are fed to the rear end of the light guide 15.

The iris diaphragm 23 is interposed between the red LED 57a, green LED 57b, and blue LED 57c and the condenser lens 28, and controlled by the diaphragm control means 24. The diaphragm control means 24 and an LED control means 56 are connected to the control means 26.

Moreover, the control means 21 incorporated in the signal processing unit 4 is connected to the control means 26. The control means 26 instructs the LED control means 56 to control glowing of the red LED 57a, green LED 57b, and blue LED 57c incorporated in the LED light source unit 52 for supplying field-sequential illumination light rays to the endoscope 2. The control means 21 controls the CCD driving means 11 and signal processing means 14 while being interlocked with glowing of the LEDs.

When the field-sequential light source unit 52 is connected to the endoscope, information indicating that a xenon lamp is used is sent from the control means 26 incorporated in the light source unit to the control means 21. When the LED light source unit 52' is connected to the endoscope, information indicating that LEDs are used is sent from the control means 26 incorporated in the light source unit to the control means 21. When a light source unit, which is not shown, including a halogen lamp is connected to the endoscope, information indicating that the halogen lamp is used is sent from the control means 26 incorporated in the light source unit. The control means 21 controls the CCD sensitivity control means 12 according to the information.

According to Example 3, even if an absolute value of the amount of emitted light differs between the light source units 52 and 52', the sensitivity of a solid-state imaging device is controlled to compensate the difference in the amount of emitted light according to information sent from a connected light source unit. This results in an endoscope system capable of producing a view image of proper brightness.

EXAMPLE 4

Figure 9:
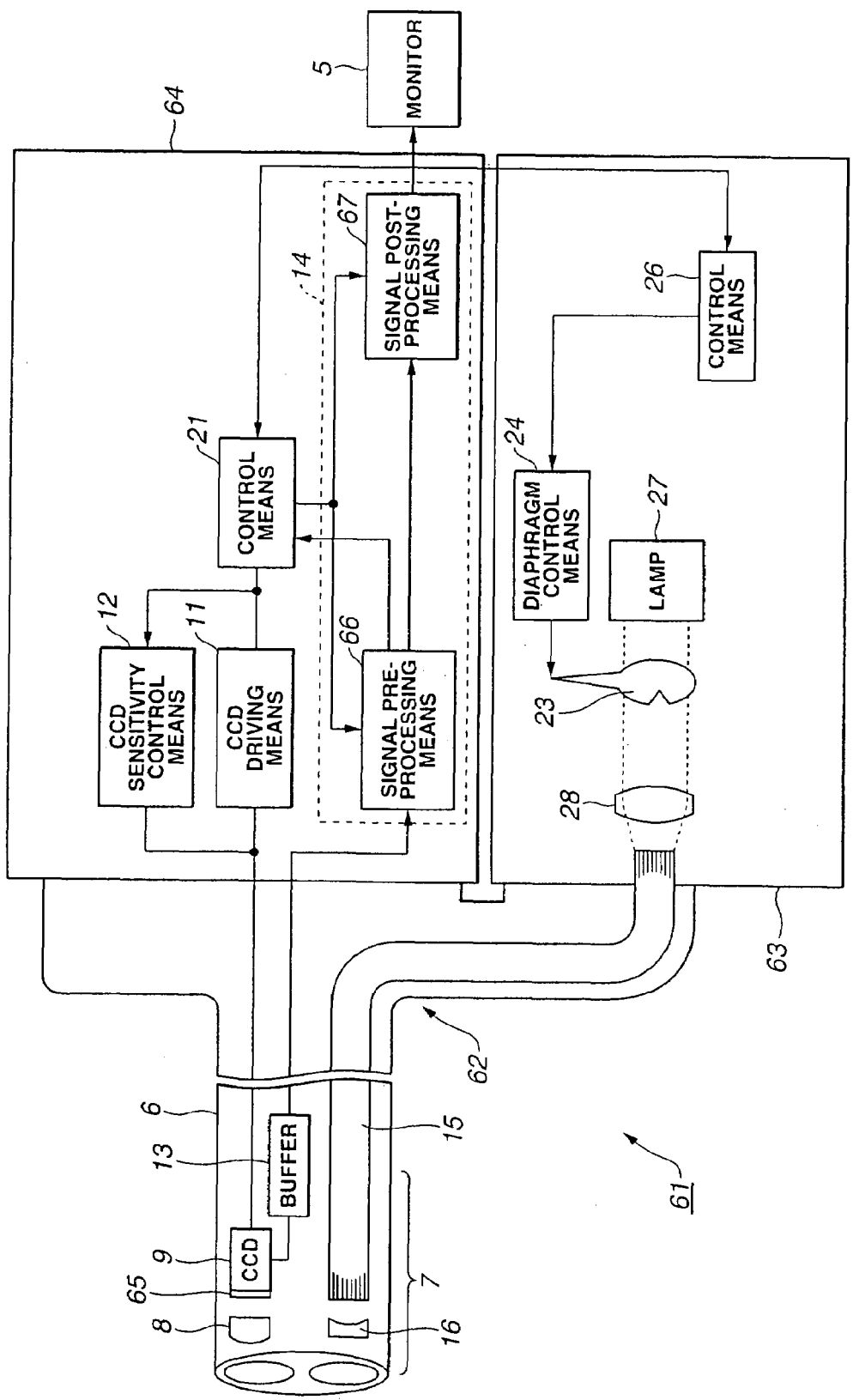
FIG. 9 is a block diagram showing the overall configuration of an endoscope system in accordance with Example 4 of the present invention.

FIG. 9 shows the configuration of an endoscope system 61 in accordance with Example 4 of the present invention. Example 4 is a simultaneous endoscope system having a color filter 65 placed on the face of the CCD 9.

The description of components identical to those shown in FIG. 1 or FIG. 7 will be omitted. Example 4 consists mainly of a simultaneous endoscope 62, a light source unit 63, a signal processing unit 64, and a monitor 5. The light source unit 63 supplies white illumination light to the endoscope 62. The signal processing unit 64 (independent of the light source unit 63) drives the CCD 9 and processes signals. An image is displayed on the monitor 5 according to a video signal output from the signal processing unit 64.

The simultaneous endoscope 62 has the color filter 65 placed on the face of the CCD 9 incorporated in the endoscope 2 included in Example 1.

The light source unit 63 does not include the RGB rotary filter 29 intervened in the path of illumination light in the field-sequential light source unit 22 shown in FIG. 1. White light emitted from the lamp 27 is converged by the condenser lens 28 through the iris diaphragm 23, and supplied to the rear end of the light guide 15. Therefore, the light source unit 63 includes neither the motor 30 shown in FIG. 1 nor the RGB rotary filter control means 25 shown therein.

Moreover, the signal processing unit 64 in Example 4 has a signal pre-processing means 66 and a signal post-processing means 67 included in the signal processing means 14 unlike the signal processing means 14 shown in FIG. 1.

Specifically, the signal processing means 14 consists of the signal pre-processing means 66 for performing various kinds of signal processing on an output signal read from the CCD 9, and the signal post-processing means 67 for performing various kinds of signal processing on an output signal of the signal pre-processing means 66 so as to output the output signal to the monitor 5. The output signal read from the CCD 9 is converted into a television signal and output to the monitor 5.

The CCD driving means 11, CCD sensitivity control means 12, and signal processing means 14 are connected to the control means 21 and controlled by the control means 21.

The control means 21 is also connected to the control means 26 for controlling the iris diaphragm 23, which is incorporated in the light source unit 63 for supplying white illumination light to the endoscope 62, and the diaphragm control means 24.

Figure 10:
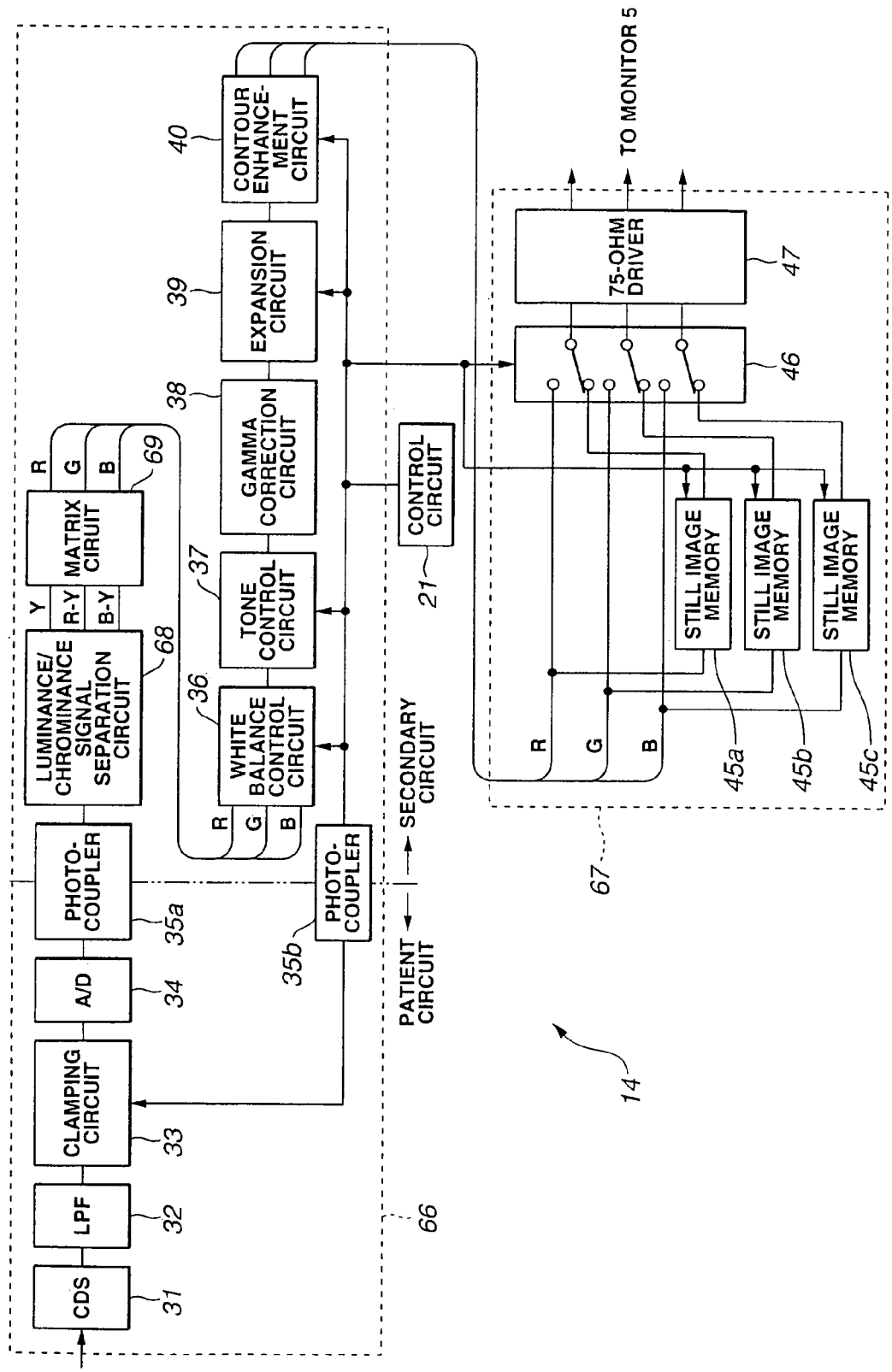
FIG. 10 is a block diagram showing in detail the configuration of a video signal processing means.

The signal processing means 14 employed in Example 4 has, for example, the configuration shown in FIG. 10. A signal output from the endoscope 62 is fed to the signal pre-processing means 66.

In the signal pre-processing means 66, an output signal of the CCD 9 having color signal components superposed on one another is digitized by the A/D converter 34 after passing through the CDS circuit 31, low-pass filter 32, and clamping circuit 33. The digital signal is isolated from a patient circuit and transmitted to a secondary circuit by the photocoupler 35a.

The output signal passing through the photocoupler 35a is split into a luminance signal Y and chrominance signals R-Y and B-Y by a luminance/chrominance signal separation circuit 68 included in the secondary circuit. The luminance signal Y and chrominance signals R-Y and B-Y are converted into red, green, and blue signals by a matrix circuit 69. The red, green, and blue signals are subjected to white balance control, tone control, and gamma correction by means of the white balance control circuit 36, tone control circuit 37, and gamma correction circuit 38. Thereafter, the red, green, and blue signals are subjected to electronic zooming by the expansion circuit 39. An output of the expansion circuit 39 is fed to the signal post-processing means 67 via the contour enhancement circuit 40.

An output of the contour enhancement circuit 40 is fed to the still image memories 45a, 45b, and 45c, in which still image signal components are stored, included in the signal post-processing means 67. The output of the contour enhancement circuit 40 is also input to the selector 46, and then fed as motion picture signal components to the monitor 5 via the 75-ohm driver 47 on the succeeding stage.

The output terminals of the still image memories 45a, 45b, and 45c are connected to the other input terminals of the selector 46. The control means 21 controls writing and reading of image signal components in and from the still image memories 45a, 45b, and 45c. In response to a Freeze instruction entered by an operator, the control means 21 controls the still image memories 45a, 45b, and 45c so that image signal components to be frozen will be stored in the memories.

Moreover, the control means 21 controls the CCD driving means 11 so that an electronic shutter will be activated in response to the Freeze instruction. The control means 21 controls the CCD sensitivity control means 12 so that the CCD sensitivity control means 12 will raise a set value of the sensitivity of the CCD. The set value of sensitivity is set to compensate a decrease in an exposure time determined by the electronic shutter. When the electronic shutter is opened for $\frac{1}{120}$ sec, the sensitivity of the CCD 9 is set to a value that is twice as large as the one set when the electronic shutter is opened for a normal exposure time of $\frac{1}{60}$ sec.

As mentioned above, according to the present example, when the electronic shutter is employed, the sensitivity of a solid-state imaging device is controlled based on the driven state of the solid-state imaging device. This results in an endoscope system capable of producing a view image of proper brightness.

VARIANT OF EXAMPLE 4

A variant of Example 4 of the present invention will be described with reference to FIG. 9 showing Example 4. The present variant is a simultaneous endoscope system connectable to both an NTSC (60 Hz) monitor and a PAL (50 Hz) monitor. The signal processing unit 64 uses a switch that is not shown to select a television system. When the NTSC system is selected, the control means 21 controls the CCD driving means 11, signal pre-processing means 66, and signal post-processing means 67 so that an image signal will be read from the CCD 9 at a rate equivalent to the frequency of 60 Hz and converted into an NTSC television signal.

When the PAL system is selected, the control means 21 controls the CCD driving means 11, signal pre-processing means 66, and signal post-processing means 67 so that an image signal will be read from the CCD 9 at a rate equivalent to the frequency of 50 Hz and converted into a PAL television signal. At this time, when the reading rates are switched, the control means 21 changes the set value of the sensitivity of the CCD 9. The control means 21 controls the CCD sensitivity control means 12 so that a video signal of the same voltage level will be produced between the reading rates equivalent to the frequencies of 60 Hz and 50 Hz.

As mentioned above, according to the present variant, when the reading rate or exposure time is changed, the sensitivity of a solid-state imaging device is controlled based oh the driven state of the solid-state imaging device. This results in an endoscope system capable of producing a view image of proper brightness.

EXAMPLE 5

Figure 11:
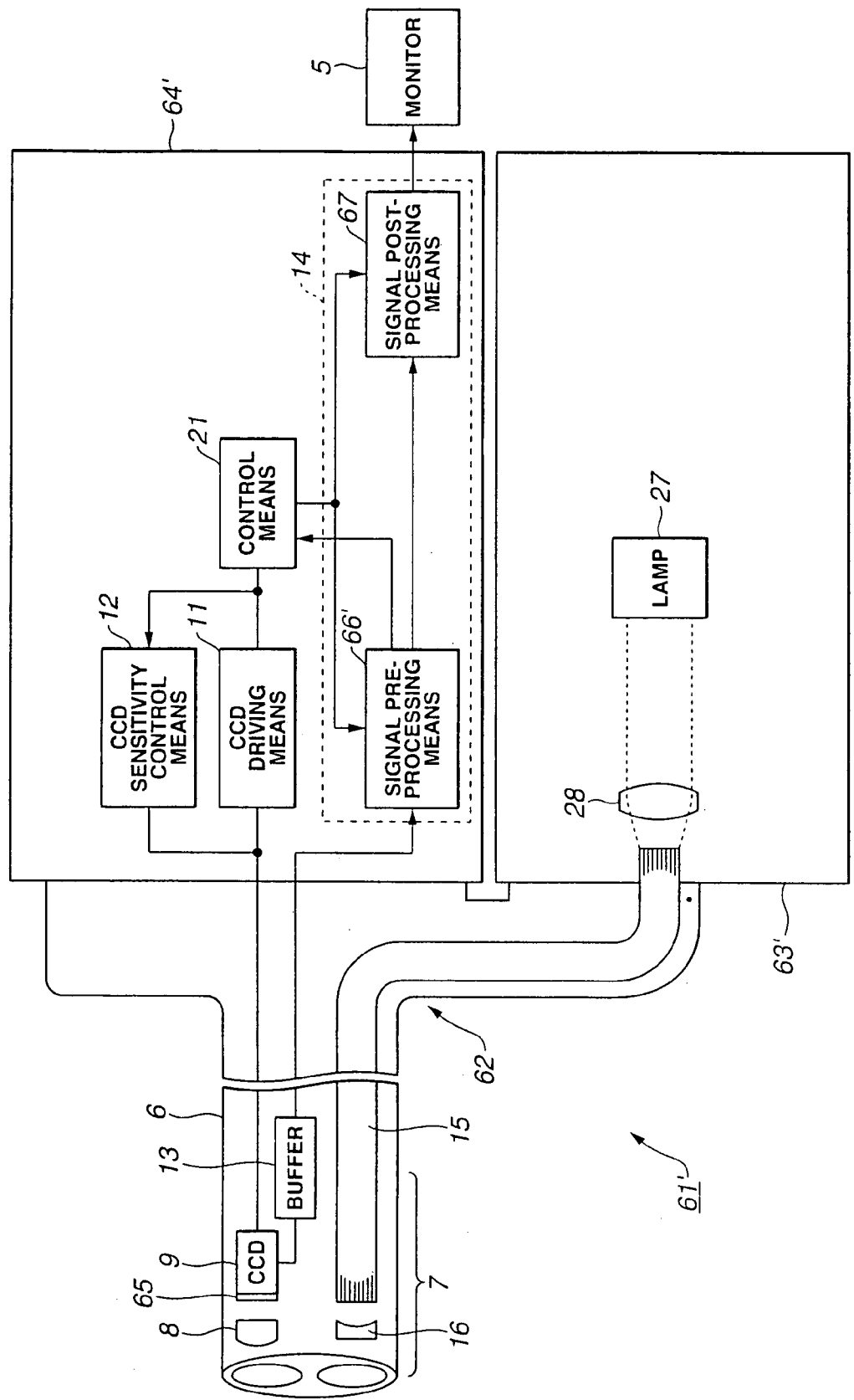
FIG. 11 is a block diagram showing the overall configuration of an endoscope system in accordance with Example 5 of the present invention.

FIG. 11 shows the configuration of an endoscope system in accordance with Example 5 of the present invention. The description of components identical to those shown in FIG. 1 or FIG. 9 will be omitted. In Example 5, an endoscope system 61' consists mainly of an endoscope 62, a light source unit 63', a signal processing unit 64, and the monitor 5.

In Example 5, the light source unit 63' does not have, unlike the light source unit 63 included in the endoscope system 61 shown in FIG. 9, the iris diaphragm 23, diaphragm control means 24, and control means 26. Illumination light emitted from the lamp 27 is converged by the condenser lens 28 and supplied to the rear end of the light guide 15.

Specifically, the light source unit 64' has no light narrowing mechanism. Irradiation light of the same amount is always fed to the rear end of the light guide 15.

Figure 12:
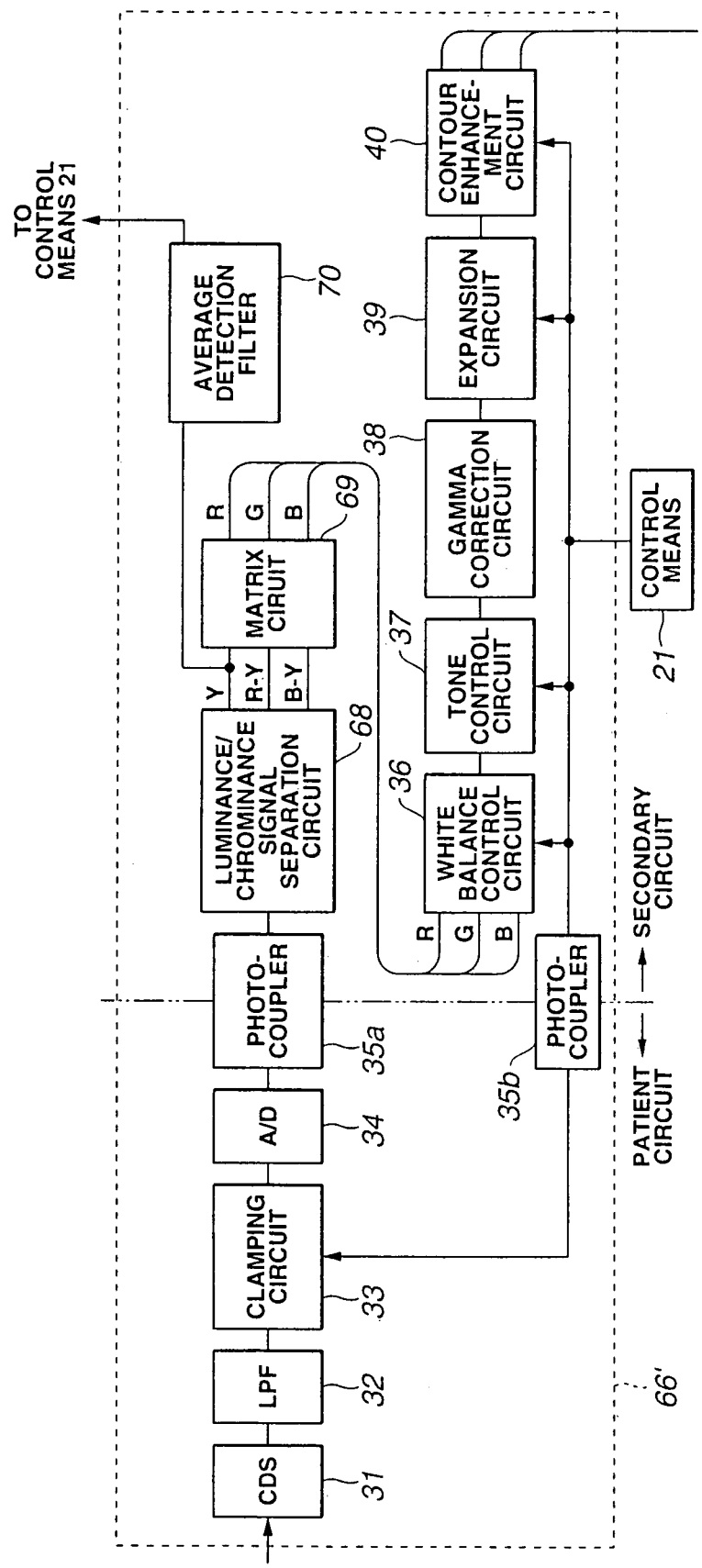
FIG. 12 is a block diagram showing in detail the configuration of a signal pre-processing means.

Moreover, the signal processing unit 64' employed in the present example has a signal processing means 14 that includes a signal pre-processing means 66' partly different from the signal pre-processing means 66 included in the signal processing means 14 of the signal processing unit 64 shown in FIG. 9. FIG. 12 shows the configuration of the signal pre-processing means 66'.

The signal pre-processing means 66' shown in FIG. 12 has, in addition to the same components as those of the signal pre-processing means 66 shown in FIG. 10, an average detection filter circuit 70 to which a luminance signal Y is input.

The average detection filter circuit 70 calculates an average of voltage levels assumed by the luminance signal Y that is one of the components of an output signal of the CCD 9 provided during one field, and sends the luminance average, to the control means 21. The control means 21 calculates the set value of the sensitivity of the CCD 9, which permits production of a view image of proper brightness, according to the luminance average, and controls the CCD sensitivity control means 12.

As mentioned above, according to the present example, the sensitivity of a solid-state imaging device is controlled based on an output signal of the solid-stage imaging device. Consequently, the endoscope system 61' can produce a view image of proper brightness. Moreover, the configuration of the light source unit 63' can be simplified.

EXAMPLE 6

Figure 13:
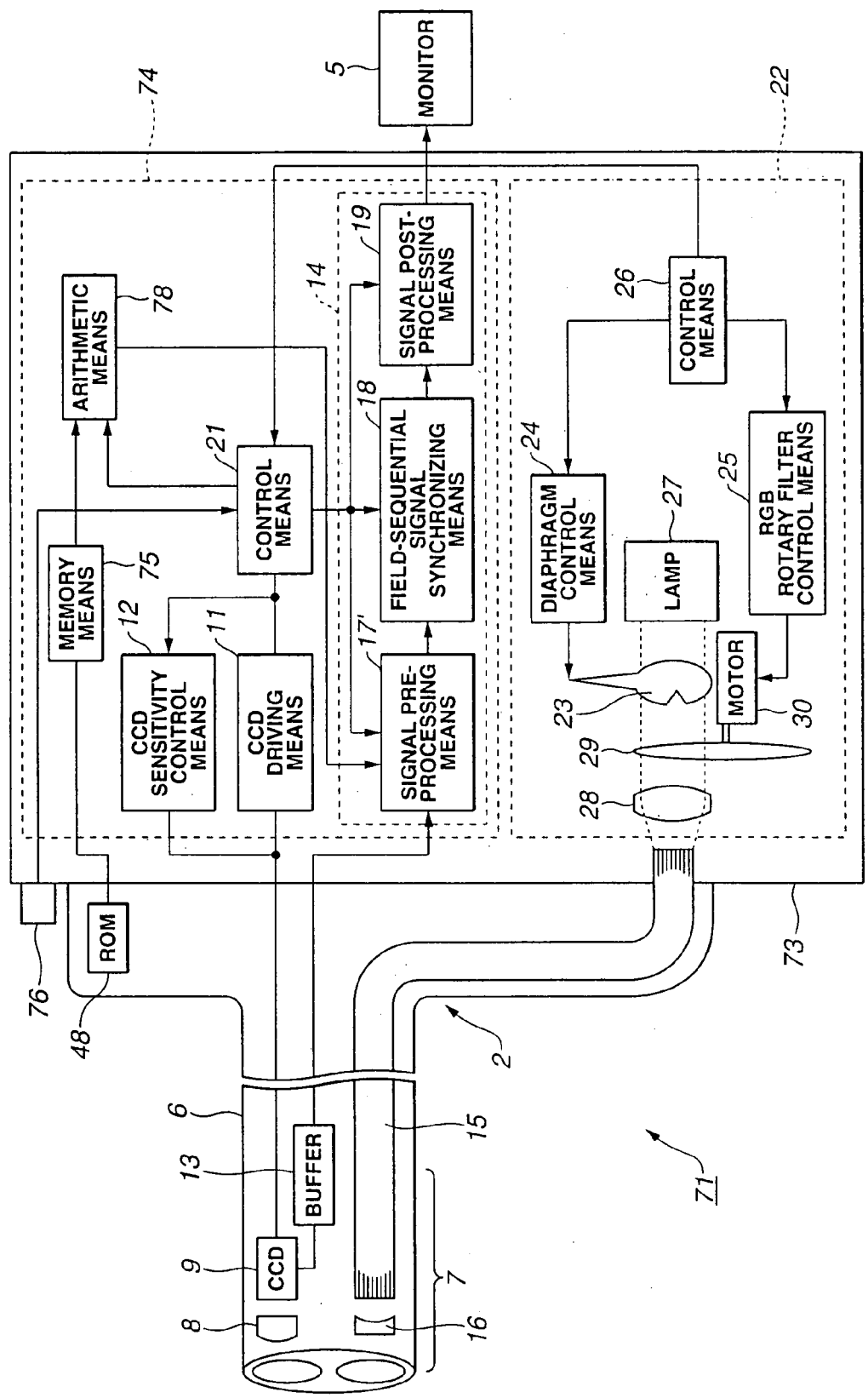
FIG. 13 to FIG. 16 are concerned with Example 6 of the present invention.

FIG. 13 shows the configuration of an endoscope system in accordance with Example 6 of the present invention. The description of components identical to those shown in FIG. 1 will be omitted.

An endoscope system 71 consists mainly of the endoscope 2, the field-sequential light source unit 22, a video processor 73 with a built-in signal processing unit 74, and the monitor 5.

According to the present example, information (data) representing a difference in an electron multiplication rate from one pixel location in the CCD 9 to another is stored in the ROM 48 incorporated in the endoscope 2.

The signal processing unit 74 employed in the present example includes, in addition to the same components as those of the signal processing unit shown in FIG. 1, a memory means 75, a switch 76, and an arithmetic means 78. Data read from the ROM 48 is stored in the memory means 75. The switch 76 is used to freely designate the sensitivity of the CCD 9. The arithmetic means 78 performs arithmetic operations to calculate correction data that compensates the above difference in the electron multiplication rate. Moreover, the signal processing means 74 includes a signal pre-processing means 17' whose configuration is partly different from the signal preprocessing means 17 shown in FIG. 1. The correction data calculated by the arithmetic means 78 is sent to the signal pre-processing means 17'. Even when the sensitivity of the CCD 9 differs from one CCD to another, the sensitivity can be set to a value designated using the switch 76.

Similarly to Example 1, when the endoscope 2 is connected to the processor 73, the information in the ROM 48 is sent to the memory means 75 incorporated in the processor 73 and stored therein. Information representing a set value of sensitivity designated using the switch 56 formed, for example, on the panel of the processor 73 and used to freely designate the sensitivity of the CCD 9 is input to the control means 21. The control means 21 controls the CCD sensitivity control means 12 according to the information.

In the present example, the number of applications of a pulse φCMD per unit time is adjusted in order to control the sensitivity. The arithmetic means 78 calculates correction data according to the difference in the electron multiplication rate from one pixel location to another, which is stored in the memory means 75, and the number of applications of the pulse φCMD per unit time.

Assuming that a reference electron multiplication rate is X, an electron multiplication rate for a certain pixel location is kX, and the number of applications of the pulse φCMD per unit time is n, the correction data for data read from the pixel location is expressed as $1/(kX)^n$.

Figure 14:
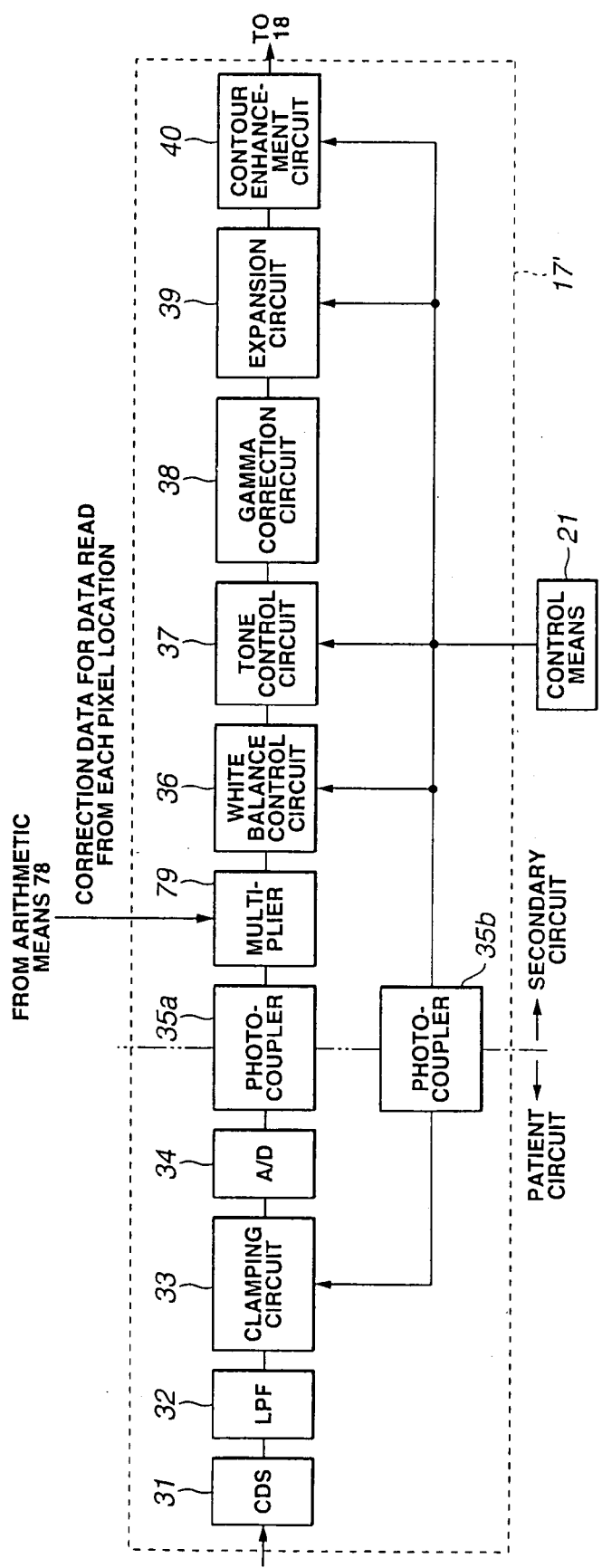

The output signal read from the CCD 9 is multiplied by the correction data for each pixel location by means of a multiplier 79 included in the signal pre-processing means 17' shown in FIG. 14. Thus, the difference in the electron multiplication rate from one pixel location to another is corrected. The resultant signal is sent to the circuit on the succeeding stage. The signal pre-processing means 17' shown in FIG. 14 has, in addition to the same components as those of the signal pre-processing means 17 shown in FIG. 2, the multiplier 79 interposed between the photocoupler 35a and white balance control circuit 36.

Figure 15:
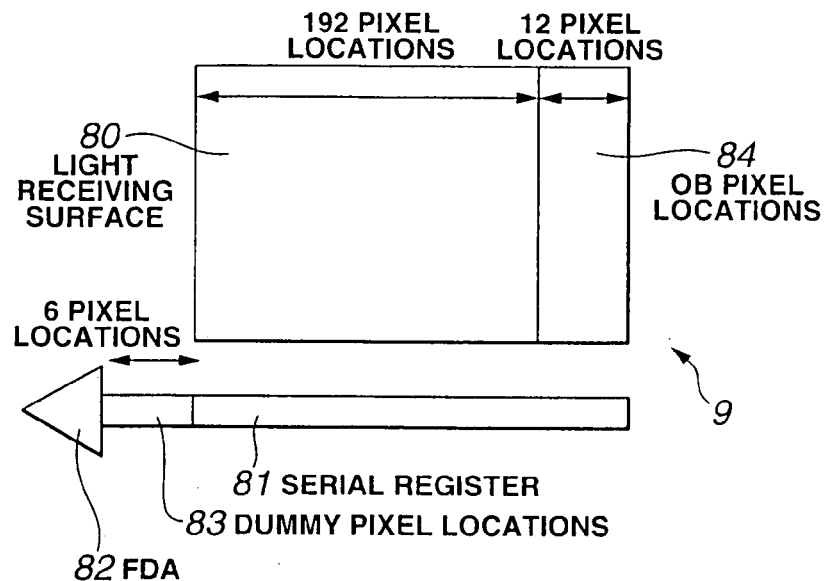

FIG. 15 shows the structure of the CCD 9 employed in the present example. A serial register 81 and an FDA 82 for converting charge into a voltage are located below a light receiving surface 80. Six dummy pixel locations 83 are preserved between the serial register 80 and FDA 82.

Based on a set value designated using the switch 76, the control means 21 extends control differently between when the CCD 9 exhibits ordinary sensitivity and when electrons flowing in the CCD are multiplied.

Figure 16A:
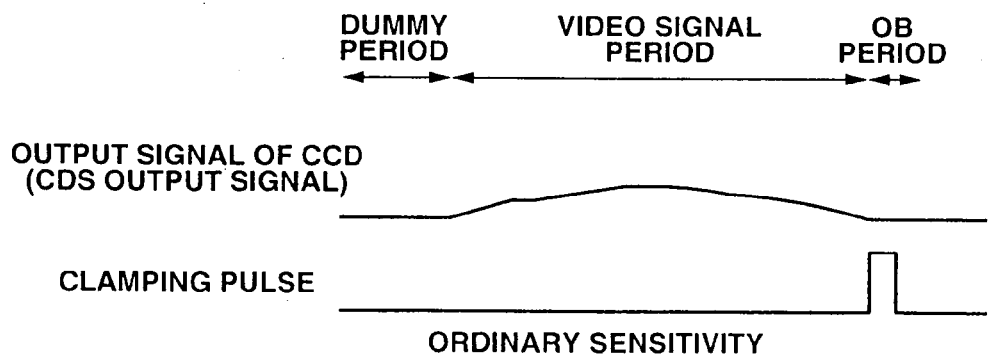

Specifically, when the electrons flowing in the CCD are not multiplied, that is, when the sensitivity of the CCD is not raised but ordinary sensitivity, the control means 21 sends a timing signal to the clamping circuit 33 according to the set value designated using the switch 76. Based on the timing signal, the clamping circuit 33 clamps an output signal of the CCD (output signal of the CDS circuit) composed of signal components read from OB pixel locations 84 during an OB period shown in FIG. 16A.

Figure 16B:
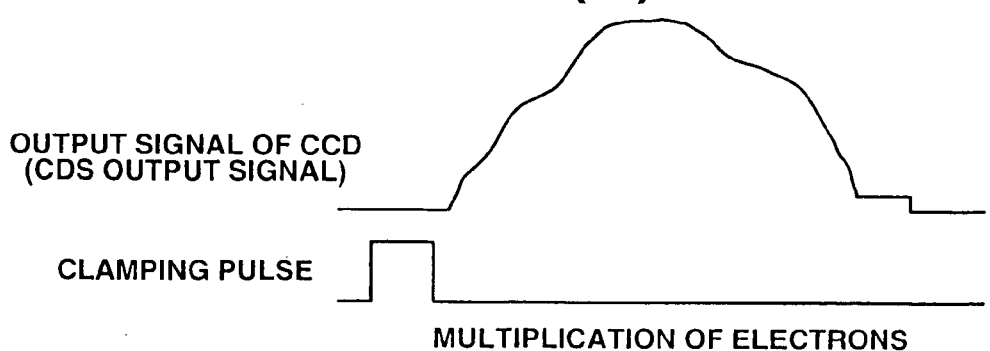

In contrast, when the electrons flowing in the CCD are multiplied in order to raise the sensitivity of the CCD, a dark current flowing in the OB pixel locations 84 is multiplied as shown in FIG. 16B. This affects a specified voltage to be clamped. For avoiding this incident, a timing signal representing a different timing of clamping is sent to the clamping circuit 33 so that the clamping circuit will clamp an output signal of the CCD composed of signal components read from the dummy pixel locations 83 during a dummy period.

As mentioned above, according to the present example, an output signal of a solid-state imaging device is corrected based on a difference in an electron multiplication rate from one pixel location in the solid-state imaging device to another and a set value of the sensitivity of the solid-state imaging device. This results in an endoscope capable of producing an excellent view image.

Moreover, the output signal of the solid-state imaging device is processed based on the set value of the sensitivity of the solid-state imaging device. Consequently, a correct black level of a gray scale is reproduced. Eventually, an excellent view image can be produced.

The description has been made on the assumption that the endoscope is an electronic endoscope having the CCD 9 incorporated in the distal part of the insertion unit 6. The present invention is not limited to this type of endoscope. The present invention can be applied to a TV camera-mounted endoscope having a TV camera, in which a CCD is incorporated, mounted on an eyepiece unit of an optical endoscope.

In this case, as described in conjunction with Example 1, for example, an input means (designating means) may be used to enter a value of the sensitivity of the CCD 9 so that the value will be fed to the control means 21. Alternatively, a feature of a TV camera may be entered together with a feature (the number of optical fibers constituting a light guide) of an optical endoscope. The control means 21 may calculate the number of applications of a sensitivity control pulse φCMD per unit time required for use of the optical endoscope and TV camera, and instruct the CCD sensitivity control means 12 to control the sensitivity of the CCD 9.

EXAMPLE 7

Figure 17:
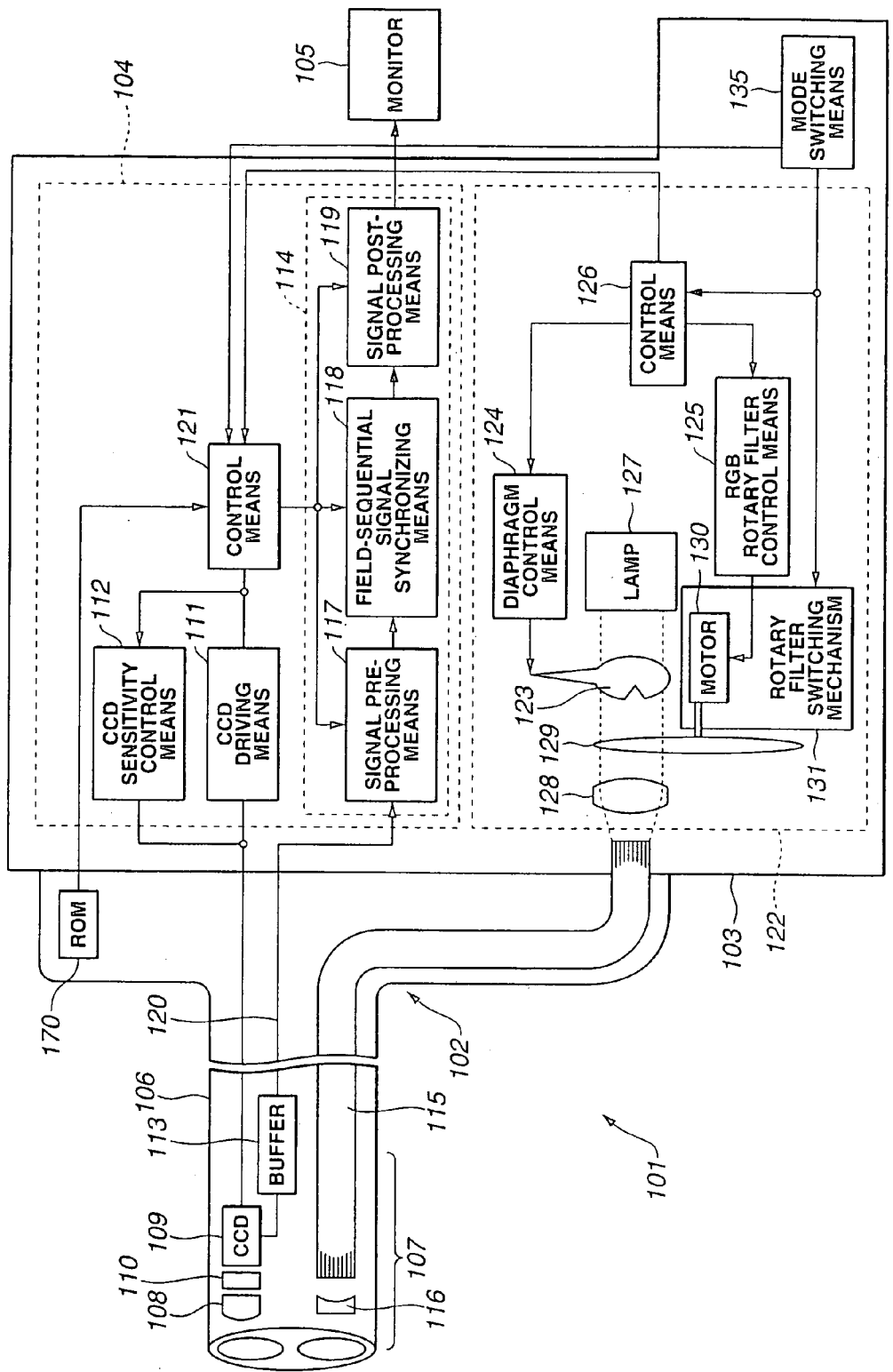
FIG. 17 to FIG. 23 are concerned with Example 7 of the present invention.
Figure 18:
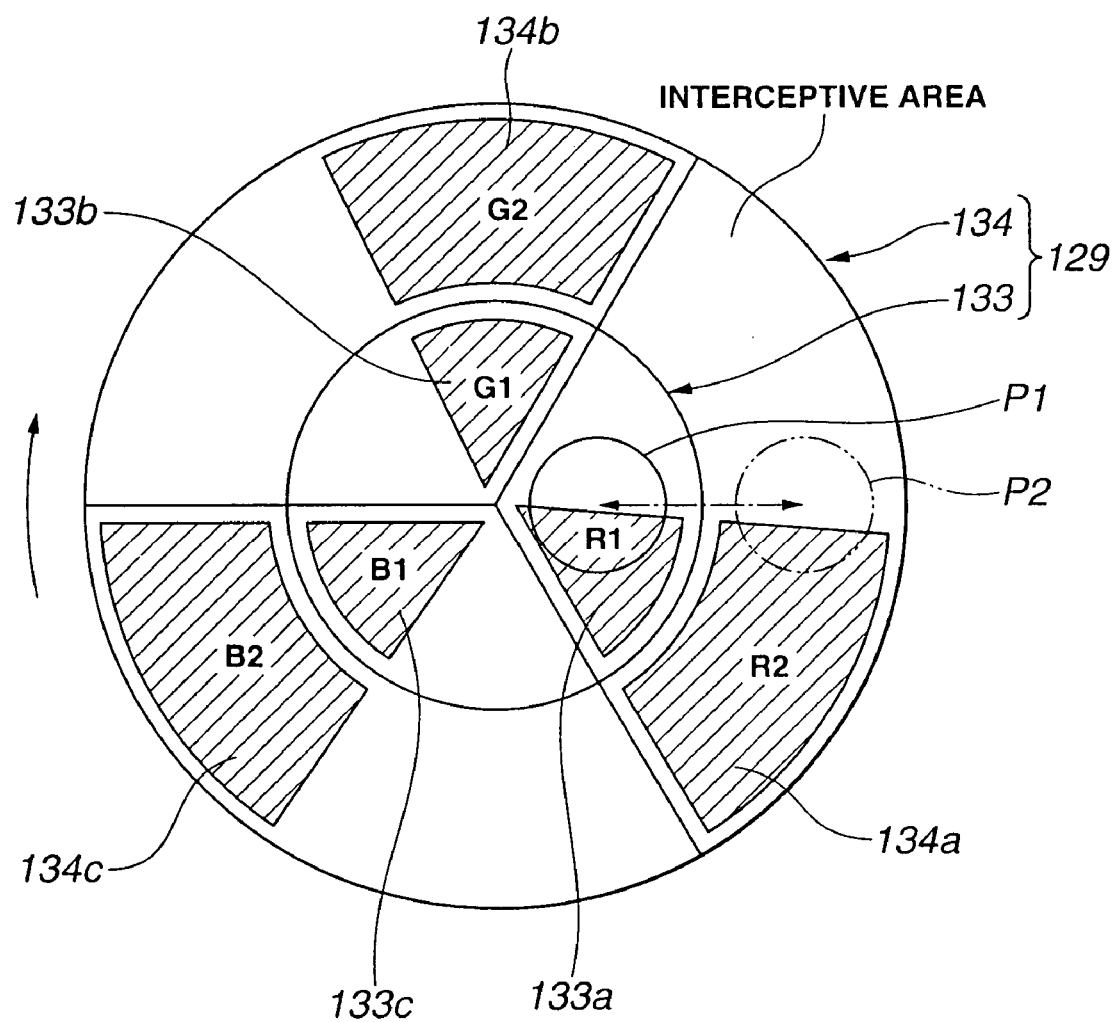
Figure 19:
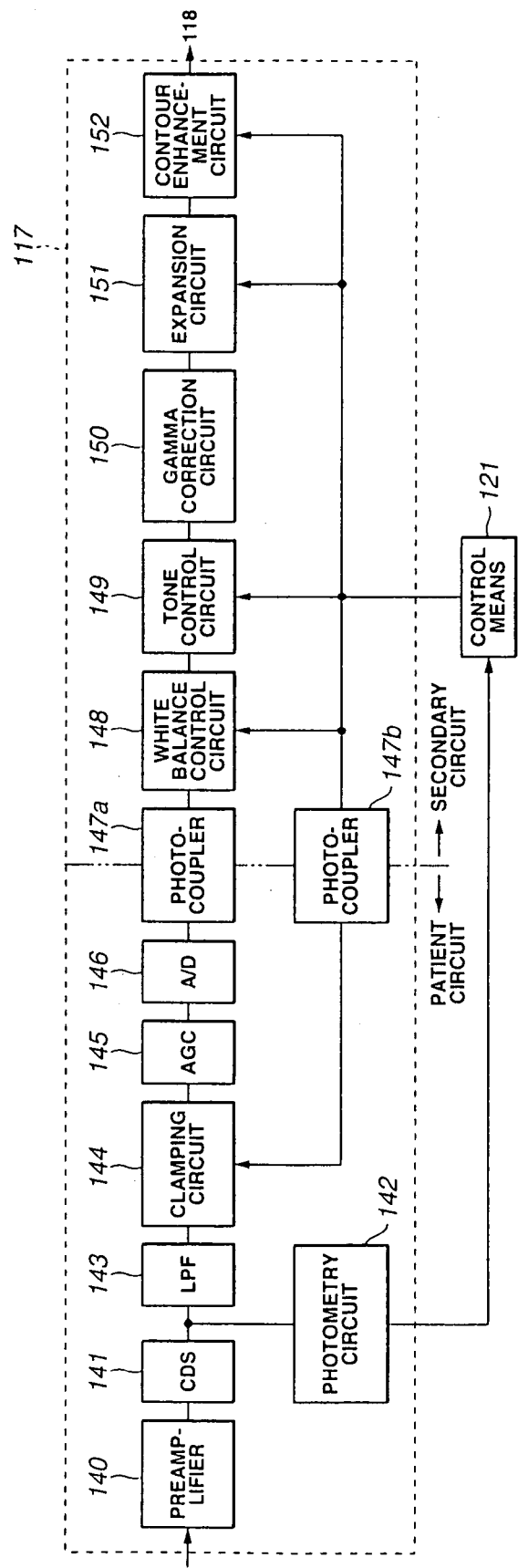
Figure 20:
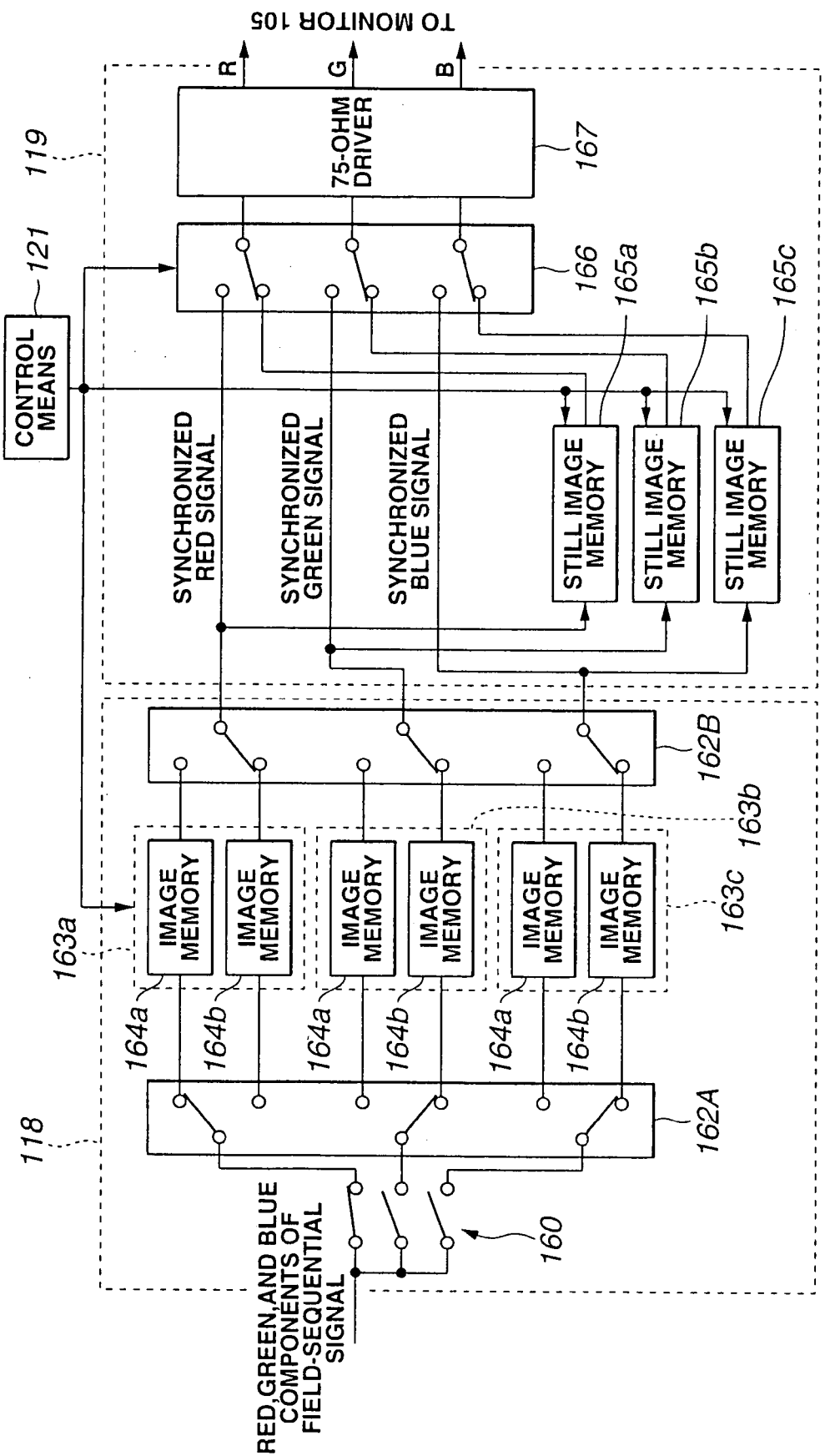
Figure 21:
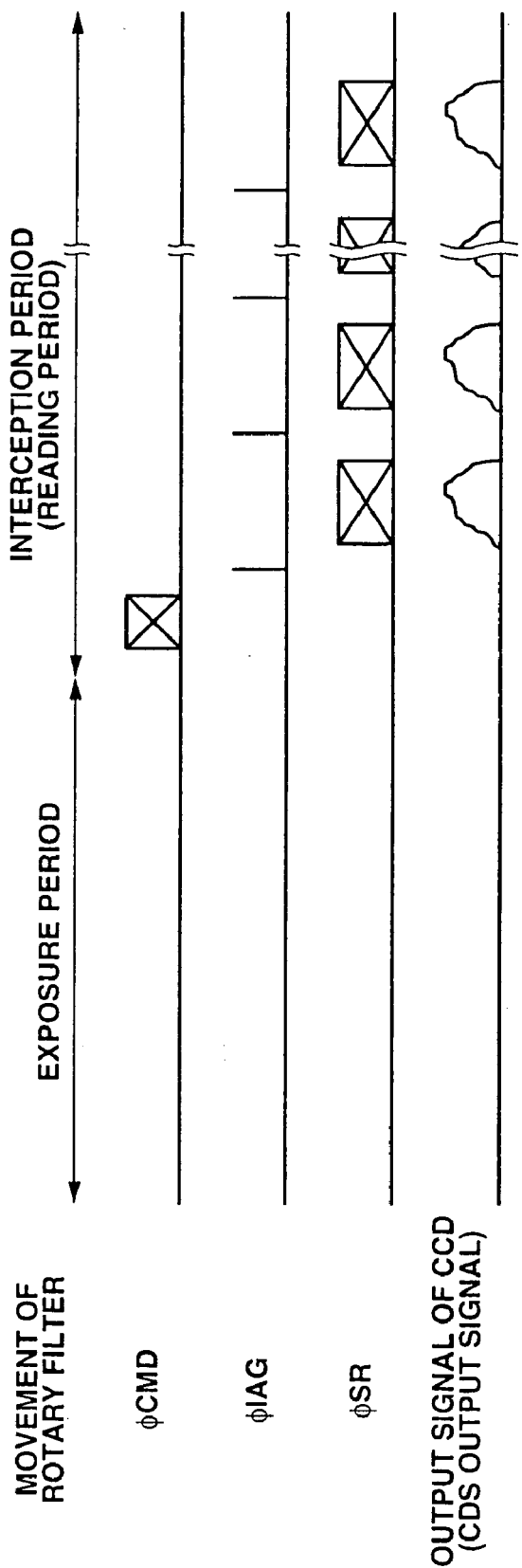
Figure 22:
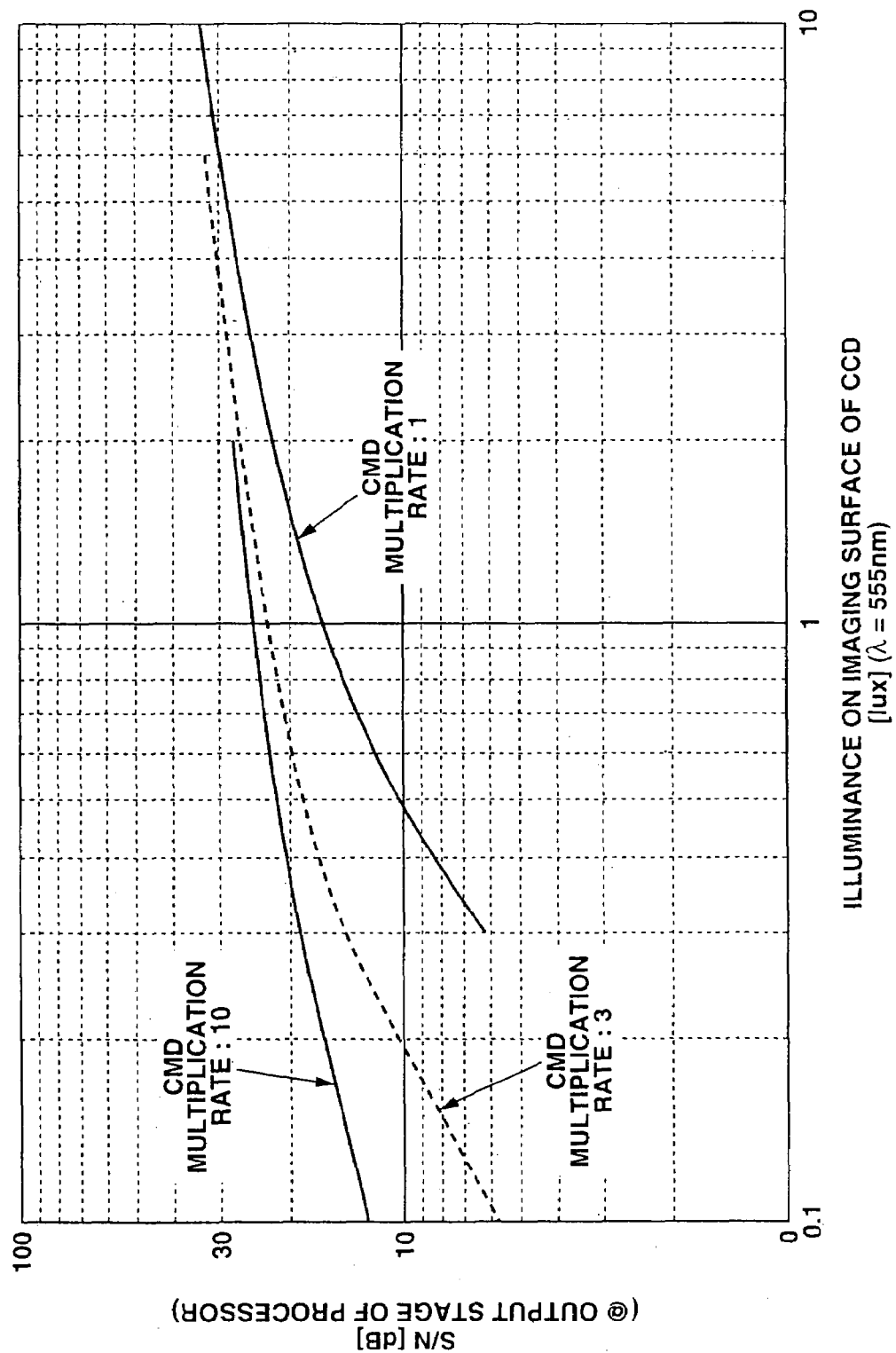
Figure 23:
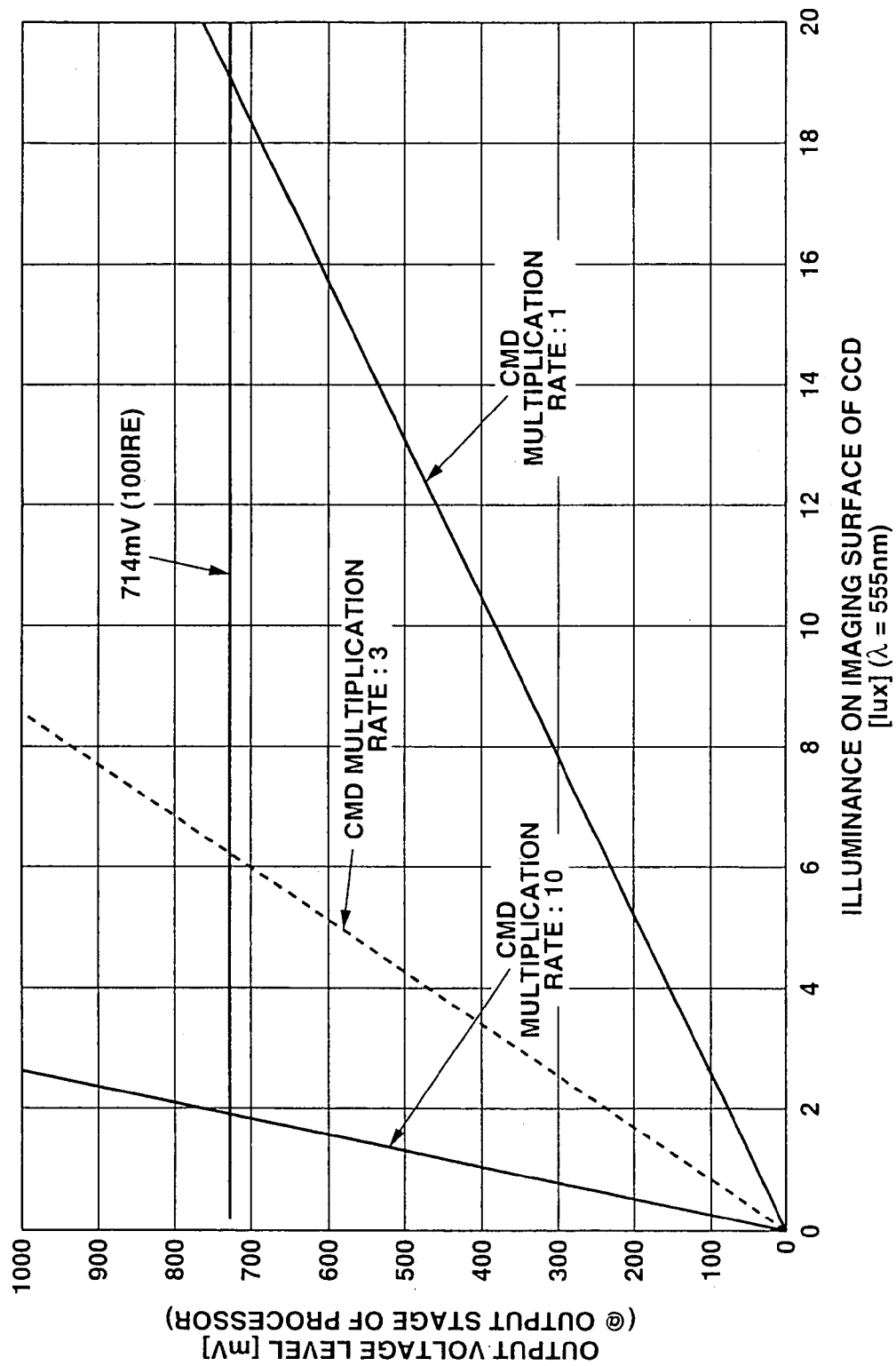

FIG. 17 to FIG. 23 are concerned with Example 7 of the present invention. FIG. 17 is a block diagram schematically showing the configuration of an endoscope system. FIG. 18 is an explanatory diagram schematically showing the arrangement of two filter sets constituting a rotary filter. FIG. 19 is a block diagram showing a signal pre-processing means included in a signal processing means. FIG. 20 is a block diagram showing a field-sequential synchronizing means and a signal post-processing means included in the signal processing means. FIG. 21 is a timing chart showing the timings of signals used to drive a CCD. FIG. 22 is a graph showing the relationship between the illuminance of an imaging surface of a CCD and a signal-to-noise ratio. FIG. 23 is a graph showing the relationship between the illuminance of the imaging surface of the CCD and an output voltage level.

As shown in FIG. 17, an endoscope system 101 of Example 7 consists mainly of an electronic endoscope (hereinafter an endoscope) 102, a processor 103, and a monitor 105. The endoscope 102 has a solid-state imaging device incorporated therein. The endoscope 102 is connected to the processor 103 so that it can be disconnected freely. A signal processing unit 104 and a field-sequential light source unit 122 are incorporated in the processor 103. The monitor 105 is connected to the processor 103. A video signal processed by the processor 103 is output to the monitor 105.

The endoscope 102 has an elongated insertion unit 106 that is inserted into a body cavity. An objective 108 through which object light is projected is incorporated in the distal part 107 of the insertion unit 106. For example, a charge-coupled device (hereinafter a CCD) 109 that is a solid-state imaging device is used as an image sensor and located on the image plane of the objective 108. The CCD 109 is connected to a CCD driving means 111 and a CCD sensitivity control means 112, which are included in the signal processing unit 104 incorporated in the processor 103, over signal lines. Exposure, multiplication of produced charge carriers, and reading are performed based on driving signals and a sensitivity control signal produced by the CCD driving means 111 and CCD sensitivity control means 112 respectively. The image sensor may be realized with a CMOS image sensor. A filter 110 for transmitting light of a certain specific wavelength band is placed on the face of the CCD 109. The filter 110 has a spectral property of transmitting light stemming from fluorescence exhibited by a living tissue but cutting off (not transmitting) excitation light.

The CCD 109 is realized with a CCD described in the U.S. Pat. No. 5,337,340 entitled "Charge Multiplying Detector (CMD) Suitable for Small Pixel CCD Image Sensors." The CCD is characterized in that an electron multiplication mechanism (that is, a charge multiplying detection (CMD)) is formed at each pixel location or as a preceding stage of a detection amplifier (as a succeeding stage of a horizontal transfer register). When an electric field (energy whose level falls within a band that is approximately 1.5 times larger than an energy gap) is induced in the electron multiplication mechanism (CMD), charge carriers (electrons) collide against electrons in the valence band of the electron multiplication mechanism. The electron multiplication mechanism is thus excited to enter a conduction band. Impact (secondary) ionization brings about a hole-electron pair. In other words, when a pulse of certain strength (amplitude) is applied sequentially, impact ionization sequentially brings about a hole-electron pair. Namely, charge carriers are multiplied to an extent proportional to the number of applications of the pulse.

The CCD 109 is connected to a signal processing means 114 incorporated in the processor 103 via a buffer 113 over a CCD cable 120 (signal line). An object image projected on the imaging surface of the CCD 109 via the objective 108 and filter 110 is converted into an electric signal by the CCD 109 and read from the CCD 109. This output signal is fed to the signal processing means 114.

FIG. 21 indicates an exposure period and an interception period (CCD reading period) determined with a rotary filter 129 to be described later. FIG. 21 also indicates the relationship among a sensitivity control pulse $\phi$CMD, a vertical transfer pulse $\phi$IAG, and a horizontal transfer pulse $\phi$SR that are applied to the CCD 109, and an output signal of the CCD. The charge multiplying detector (CMD) may be located at each pixel location in the CCD 109 or as a preceding stage of a detection amplifier therein. Herein, the CMD shall be located at each pixel location. The sensitivity (CMD multiplication rate) of the CCD 109 can be controlled by adjusting either the number of applications of the pulse $\phi$CMD per unit time or the amplitude (voltage level) thereof. Herein, the number of applications of the pulse $\phi$CMD per unit time is adjusted to attain desired sensitivity (CMD multiplication rate). In this case, the sensitivity control pulse $\phi$CMD is applied to the CCD 109 during the interception period (reading period) succeeding the exposure period, whereby the sensitivity (CMD multiplication rate) of the CCD 109 is raised. Produced charge carriers are multiplied. Thereafter, the vertical transfer pulse $\phi$IAG and horizontal transfer pulse $\phi$SR are applied to the CCD 109. An output signal of the CCD 109 is then acquired. Namely, the number of applications of the sensitivity control pulse $\phi$CMD per unit time is varied in order to enable the CCD 109 to exert desired sensitivity (CMD multiplication rate).

The endoscope 102 has a light guide 115 over which illumination light of wavelengths ranging from the ultraviolet spectrum to the near-infrared spectrum can be propagated. An illumination lens 116 is located in front of the distal end of the light guide 115. Illumination light that may be ordinary light or special light propagated through the endoscope 102 over the light guide 115 is irradiated to an object through the illumination lens 116. An SLF fiber (product name) or a quartz fiber may be used to realize the light guide 115.

The signal processing means 114 consists of a signal pre-processing means 117, a field-sequential synchronizing means 118, and a signal post-processing means 119. The signal pre-processing means 117 performs various kinds of processing on an output signal read from the CCD 109. The field-sequential synchronizing means 118 synchronizes field-sequential signal components output from the signal pre-processing means 117. The signal post-processing means 119 performs various kinds of processing on an output signal of the field-sequential synchronizing means 118, and outputs the signal to the monitor 105. In short, the output signal read from the CCD 109 is converted into a television signal and output to the monitor 105.

The CCD driving means 111, CCD sensitivity control means 112, and signal processing means 114 are connected to a (first) control means 121. The control means 121 extends control. The control means 121 is connected to a (second) control means 126 for controlling an iris diaphragm 123, a diaphragm control means 124, and an RGB rotary filter control means 125 which are included in a field-sequential light source unit 122 for routing field-sequential illumination light rays to the endoscope 102. The control means 121 controls the CCD driving means 111 and signal processing means 114 while being interlocked with the RGB rotary filter control means 125.

The field-sequential light source unit 122 includes a lamp 127, a condenser lens 128, and an RGB rotary filter 129. The lamp 127 generates illumination light of wavelengths falling within a wide band that ranges from the ultraviolet spectrum to the infrared spectrum. The condenser lens 128 converges the illumination light on the rear end of the light guide 115. The RGB rotary filter 129 is interposed between the lamp 127 and condenser lens 128. A xenon lamp, a halogen lamp, a metal halide lamp, an LED, or a high-pressure mercury lamp may be used as the lamp 127.

The rotary filter 129 is attached to the rotation shaft of a motor 130 so that it can rotate. The rotary filter 129 is controlled to rotate at a specified rotating speed by the RGB rotary filter control means 125 under control of the control means 126. Field-sequential light rays of red, green, and blue are routed to the rear end of the light guide 115.

The rotary filter 129 consists of two filter sets as shown in FIG. 18, that is, a pair of filter sets 133 and 134 formed as an inner circumferential part and outer circumferential part. The inner circumferential first filter set 133 consists of three filters that pass light rays R1, G1, and B1 required for an ordinary light mode (observation under ordinary light). The outer circumferential second filter set 134 consists of three filters that pass light rays R2, G2, and B2 required for a special light mode (observation under special light). The first filter set 133 and second filter set 134 each have a spectral property of transmitting light suitable for each purpose of observation. The first filter set 133 has filters 133a, 133b, and 133c, which pass red (R1), green (G1), and blue (B1) light rays required for the ordinary light mode (observation under ordinary light), shaped like sectors and arranged circumferentially discretely. Filters 134a, 134b, and 134c that pass red (R2), green (G2), and blue (B2) light rays required for the special light mode (observation under special light) are discretely arranged outside the filters 133a, 133b, and 133c respectively.

Portions of the first filer set 133 among the filters 133a, 133b, and 133c that pass the red (R1), green (G1), and blue (B1) rays required for the ordinary light mode (observation under ordinary light) are interceptive areas. The interceptive areas determine the interception period (reading period) during which the CCD 109 is read. The filters 133a, 133b, and 133c and the interceptive areas are arranged nearly equidistantly. The same applies to the second filter set 134.

The filter 134b is realized with an excitation filter that passes light of wavelengths ranging from the ultraviolet spectrum to the blue spectrum and being used in the special light mode. The light passing through the filter 134b causes a living tissue to exhibit fluorescence. The filters 134a (R2) and 134c (B2) are blocked in the present example, and no light passes through these filters.

A rotary filter switching mechanism 131 is disposed on the ray axis of illumination light linking the lamp 127 and light guide 115 in order to select either the inner circumferential filter set 133 or outer circumferential filter set 134. In the ordinary light mode, light P1 emanating from the lamp 127 (indicated with a solid line in FIG. 18) falls on the inner circumferential filter set 133. In the special light mode, the rotary filter mechanism 131 switches the filter sets by moving the whole rotary filter 129 so that light P2 (indicated with a dot-dash line in FIG. 22) will fall on the outer circumferential filter set 134. The rotary filter switching mechanism 131 moves the motor 130 and rotary filter 129 relatively to the lamp 127. Alternatively, the lamp 127 may be moved in an opposite direction.

The processor 103 is connected to a mode switching means 135. When it is instructed to switch the observation modes (ordinary light mode and special light mode), a rotary filter switching instruction signal is fed to the rotary filter switching mechanism 131 and control means 126. When the filter sets of the rotary filter 129 are switched, if the special light mode is selected, the iris diaphragm 123 is automatically fully closed by the diaphragm control means 124.

The rotary filter switching instruction signal is also fed to the control means 121. The control means 121 controls the signal processing means 114, CCD driving means 111, and CCD sensitivity control means 112 so that these means will act in a selected mode (ordinary light mode or special light mode).

The signal processing means 114 has the signal pre-processing means 117 thereof configured as shown in, for example, FIG. 19. Referring to FIG. 19, an output signal of the CCD 109 is fed to the signal pre-processing means 117. In the signal pre-processing means 117, the output signal of the CCD 109 passes through a preamplifier 140, a CDS circuit 141, a low-pass filter 143, a clamping circuit 144, an automatic gain control (AGC) circuit 145. An A/D converter 146 then digitizes the signal. The digital signal is isolated from a patient circuit and transmitted to a secondary circuit by a photocoupler 147a. The secondary circuit includes a white balance control circuit 148, a tone control circuit 149, and a gamma correction circuit 150. After white balance control, tone control, and gamma correction are carried out, an expansion circuit 151 performs electronic zooming for the purpose of expansion.

An output signal of the expansion circuit 151 is fed to the field-sequential synchronizing means 118 via a contour enhancement circuit 152. A photometry means 142 is connected as a succeeding stage of the CDS circuit 141. An average of voltage levels assumed by the output signal of the CCD 109 during one field is calculated and fed to the control means 121. The control means 121 outputs a control signal to each of the white balance control circuit 148, tone control circuit 149, expansion circuit 151, and contour enhancement circuit 152 which are included in the secondary circuit. Moreover, the control means 121 outputs a control signal, which is used to control the clamping circuit 144 included in the patient circuit, via the photocoupler 147b serving as an isolation/transmission means.

The red, green, and blue field-sequential signal components output from the signal pre-processing means 117 are fed to synchronizing means 163a, 163b, and 163c via selector switches 160, 162A, and 162B included in the field-sequential signal synchronizing means 118 shown in FIG. 20. The synchronizing means 163a, 163b, and 163c each have a memory in which data for at least one field can be stored. The red, green, and blue field-sequential signal components that are fed in that order are stored in the memories associated with the colors. The stored field-sequential signal components are read simultaneously, and output as synchronized signal components.

FIG. 20 shows synchronizing means 163I (where I denotes a, b, or c) as an example of the synchronizing means 163a, 163b, and 163c. The synchronizing means 163I is each realized with a means composed of image memories 164a and 164b in which data for at least two fields can be stored. The synchronizing means 163a is associated with a video signal component acquired with light passing through the filter 133a or 134a of the rotary filter 129. Likewise, the synchronizing means 163b is associated with a video signal component acquired with light passing through the filter 133b or 133a of the rotary filter 129. The synchronizing means 163c is associated with a video signal component acquired with light passing through the filter 133c or 134c of the rotary filter 129.

Writing and reading of an image signal component in and from the image memories 164a and 164b are switched alternately, whereby signal components are synchronized. Synchronized signal components output from the synchronizing means 163a, 163b, and 163c are fed to still image memories 165a, 165b, and 165c, in which still image signal components are stored, included in the signal post-processing means 119, and also fed to a selector 166. The synchronized signal components output from the synchronizing means 163a, 163b, and 163c pass through the selector 166, and are fed as motion picture signal components to the monitor 105 via a 75-ohm driver 167 disposed as a succeeding stage of the selector 166. The other input terminals of the selector 166 are connected to the still image memories 165a, 165b, and 165c.

The control means 121 controls writing and reading of an image signal component in and from the still image memories 165a, 165b, and 165c. In response to an external Freeze instruction, the control means 121 extends control so that image signal components to be frozen will be stored in the still image memories 165a, 165b, and 165c respectively. Moreover, the control means 121 controls the selector 166 so that the selector will feed still image signal components, which are output from the still image memories 165a, 165b, and 165c, to the monitor 105 via the 75-ohm driver 167 on the succeeding stage of the selector. Herein, the selector 166 selects either of the still image signal components and the motion picture signal components output from the synchronizing means 163a, 163b, and 163c.

A ROM 170 in which information inherent to the endoscope 102 is stored is incorporated in the endoscope 102. When the endoscope 102 is connected to the processor 103, the information is transmitted to the control means 121 included in the signal processing unit 104 incorporated in the processor 103. The sensitivity (CMD multiplication rate) of the CCD 109 is then controlled. In short, the ROM 170 serves as a designating means for designating the sensitivity of the CCD 109.

(Operations)

Operations to be exerted in the ordinary light mode and special light mode will be described below.

To begin with, assume that the ordinary light mode (observation under ordinary light) is designated. In this case, the first filter set 133 of the rotary filter 129 is placed on the path of illumination light. The CMD multiplication rate for the CCD 109 is set to a fixed value. The set value (fixed value) of the CMD multiplication rate for the CCD 109 predefined for the ordinary light mode is transmitted from the ROM 70 to the processor 103 when the endoscope 102 is connected to the processor 103.

The CCD sensitivity control means 112 receives the set (fixed) value of the CMD multiplication rate for the CCD 109, which is transmitted from the ROM 70, via the control means 121. The CCD sensitivity control means 112 calculates the number of applications of a pulse per unit time associated with the set (fixed) value of the CMD multiplication rate predefined for the ordinary light mode. The CCD sensitivity control means 112 then outputs the calculated number of applications of the pulse per unit time to the CCD 109 during an exposure period or an interception (reading) period during which the CCD 109 receives light or is read.

An input means (or designating means) such as a keyboard may be connected to the control means 121 included in the signal processing unit 104. A user may manually enter any value as the CMD multiplication rate at the input means. In this case, the CCD sensitivity control means 112 sets the CMD multiplication rate for the CCD 109 to the user-entered value under control of the control means 121. The same applies to the special light mode.

Illumination light emitted from the lamp 127 passes through the first filter set 133. Red, green, and blue field-sequential illumination light rays are successively irradiated to a living tissue. Reflected rays of the red, green, and blue rays are projected on the CCD 109, and red, green, and blue image signal components (video signal components) are input to the signal processing means 114. Consequently, a view image produced with ordinary light is displayed on the monitor 105.

The photometry means 142 calculates an average of voltage levels assumed by an output signal of the CCD 109 during one field, and outputs the average to the control means 121. The control means 121 outputs the average to the second control means 126. A diaphragm control command is output based on the average, whereby the iris diaphragm 123 is opened or closed. If an object is too bright relative to a predefined reference brightness level, the output signal of the CCD 109 assumes a high voltage level. Consequently, the iris diaphragm 123 is closed (the intensity of light routed to the rear end of the light guide decreases). In contrast, if the object is dark, the output signal of the CCD 109 assumes a low voltage level. Consequently, the iris diaphragm 123 is opened (the intensity of light routed to the rear end of the light guide increases). Thus, the intensity of light irradiated to a living tissue is varied (automatic light adjustment).

When an input means (or designating means) such as a keyboard is connected to the control means 121 included in the signal processing unit 104, a user can set the brightness (reference value) of an image displayed on the monitor 105 to any level at the input means. The automatic gain control circuit 145 can electrically amplify the output signal of the CCD 109 so that the brightness of an image displayed on the monitor 105 will be set to the designated level. When an object is too dark, even if the automatic light adjustment is performed, the brightness of an image displayed on the monitor 105 may not reach the designated level. In this case, the output signal of the CCD 109 is electrically amplified (automatic gain control).

The intensity of reflected light of (red, green, and blue) field-sequential light rays irradiated to a living tissue (alimentary canal or bronchus) falls within a domain larger than 1 lux in the graphs of FIG. 22 and FIG. 23. As seen from FIG. 22 and FIG. 23, when the CMD multiplication rate for the CCD 109 is set to a larger value, a signal-to-noise ratio and an output voltage level are higher than those attained when electrons flowing in each CMD in the CCD 109 are not multiplied.

Assume that the ordinary light mode (observation under ordinary light) is designated. In this case, even if the brightness of an object (living tissue), or in other words, the intensity of light reflected from an object varies, a view image of proper brightness whose level is designated by a user is always displayed on the monitor 105. This is attributable to the automatic light adjustment and automatic gain control. Moreover, when the CMD multiplication rate for the CMD 109 is raised, the signal-to-noise ratio improves. Namely, in the ordinary light mode (observation under ordinary light), a view image of proper brightness can be produced without impairment of image quality owing to the automatic light adjustment. If the automatic light adjustment fails to provide sufficient brightness, the automatic gain control is activated.

In contrast, assume that the special light mode (observation under special light) is designated. In this case, a user manipulates, for example, a mode selection switch included in the mode switching means 135. The rotary filter switching mechanism 131 is thus activated to place the second filter set 134 of the rotary filter 129 on the path of illumination light. At this time, the iris diaphragm 129 is fully opened. Consequently, the most intense excitation light falls on the rear end of the light guide 115. The sensitivity of the CCD 109, that is, the CMD multiplication rate for the CCD 109 is set to a fixed value predefined for the special light mode. The set value (fixed value) of the CMD multiplication rate for the CCD 109 is a value transmitted from the ROM 170 and is larger than that predefined for the ordinary light mode (observation under ordinary light).

The CCD sensitivity control means U2 receives the set (fixed) value of the CMD multiplication rate for the CCD 109 from the ROM 170 via the control means 121. The CCD sensitivity control means then calculates the number of applications of a pulse associated with the set (fixed) value of the CMD multiplication rate predefined for the special light mode. The CCD sensitivity control means outputs the calculated number of applications of the pulse to the CCD 109 during an exposure or interception (reading) period during which the CCD 109 receives light or is read.

Excitation light (of wavelengths ranging from the ultraviolet spectrum to the blue spectrum in the present example) emitted from the lamp 127 passes through the second filter set 134. In the present example, only excitation light passing through the filter 134b (G2) is irradiated intermittently to a living tissue. In the present example, the filters 134a (R2) and 134c (B2) are blocked. No light therefore passes through the filters 134a (R2), and 134c (B2).

Light reflected from a living tissue to which excitation light is irradiated, and light stemming from fluorescence exhibited by (for example, NADH or flavin contained in) the living tissue excited by the excitation light falls on the objective 108. The filer 110 cuts off the reflected light of the excitation light. The light stemming from fluorescence enters the CCD 109. An image signal picked up from the light stemming fluorescence by the CCD 109 is fed to the signal processing means 114. The signal processing means 114 processes the image signal derived from the light passing through the filter 134b (G2), and outputs the resultant signal to the monitor 105.

The automatic gain control circuit 145 electrically amplifies the output signal of the CCD 109 to a set voltage level. Specifically, assume that an object is so dark that the output signal of the CCD 109 is still lower than the set voltage level despite multiplication of electrons flowing in each CMD in the CCD 109. In this case, the output signal is electrically amplified in order to increase the magnitude of the output signal (automatic gain control). Consequently, a view image of proper brightness produced with special light can always be displayed on the monitor 105. Incidentally, when an input means (or designating means) such as a keyboard is connected to the control means 121 included in the signal processing unit 104, a user can set the brightness (aforesaid reference level) of an image displayed on the monitor 105 to any level at the input means.

Now, a description will be made of a signal-to-noise ratio relative to a signal representing a view image (in the present example, an image produced with light stemming from fluorescence) displayed on the monitor 105, and the brightness of the view image. The signal-to-noise ratio and brightness are attained with the CMD multiplication rate for the CCD 109 raised (set to be 3 or 10) (see FIG. 22 and FIG. 23).

The signal-to-noise ratio reflects how well a dark object can be visualized or with what image quality the dark object can be visualized. Especially when an image signal is picked up from feeble light such as light stemming from fluorescence, the signal-to-noise ratio relative to the image signal is a very important parameter. Moreover, the output voltage level of the image signal reflects the brightness of an image displayed on a monitor, and is therefore a very important parameter, too. When a solid-state imaging device employed is a typical CCD (without a multiplication mechanism), the signal-to-noise ratio relative to a signal representing a view image to be display on the monitor 105 and the brightness of the view image substantially correspond to those attained when the CMD multiplication rate for the CCD 109 is set to 1 (electrons flowing in each CMD in the CCD 109 are not multiplied).

When light of wavelengths ranging from the ultraviolet spectrum to the blue spectrum is irradiated to a living tissue (alimentary canal or bronchus), light stems from fluorescence exhibited by NADH, flavin, or collagen contained in the living tissue. However, the intensity of the light stemming from fluorescence is very low (falls within a domain smaller than 1 lux in the graphs of FIG. 22 and FIG. 23). It is hard for a typical CCD to pick up an image signal from such light. As seen from FIG. 22 and FIG. 23, when the CMD multiplication rate for the CCD 109 is set to a higher value, the signal-to-noise ratio and output voltage level are much higher than they are when the typical CCD is employed.

The relationship among the illuminance (reflecting the brightness of an object) of an imaging surface of the CCD 109, a signal-to-noise ratio detected on an output stage of the processor 103, and an output voltage level detected thereon will be described in relation to the sensitivity of the CCD 109. Assume that an endoscope system concerned includes the endoscope 101 (including the CCD 109 and CCD cable 120) and the processor 103 (including the signal processing means 114). The signal-to-noise ratio S/N and output voltage level S detected on the output stage (signal processing means 114) of the processor 103 are calculated theoretically.

$$S/N = S/\{N\ CCD^2 + N\ CV^2\}^{1/2} \quad (1)$$

$$= \{A \cdot n \cdot K \cdot (1-\beta) \cdot G\}/ \quad (1\text{-}2)$$
$$\{(A^2 \cdot F^2 \cdot (n+D) + R^2) \cdot K^2 \cdot (1-\beta)^2 \cdot G^2 + N\ CV^2\}^{1/2}$$

$$= \{n \cdot K \cdot (1-\beta) \cdot G\}/\{(F^2 \cdot (n+D) + R^2/A^2\} \cdot \quad (1\text{-}3)$$
$$K^2 \cdot (1-\beta)^2 \cdot G^2 + N\ CV^2/A^2\}^{1/2}$$

$$S = A \cdot n \cdot K \cdot (1-\beta) \cdot G\ [mV] \quad (2)$$

where S denotes the output voltage level of an image signal (detected on the output stage of the processor 103). Herein, for brevity's sake, the pedestal level of the signal shall be 0. Moreover, N CCD denotes the voltage level of a noise occurring in the CCD 109 (detected on the output stage of the processor 103). N CV denotes the total voltage level of a noise occurring along the CCD cable 120 and a noise occurring in the processor 103 (detected on the output stage of the processor 103).

[Parameters]

(1) CCD-Related Parameters n [e/pixel]: the number of charge carriers per pixel location (before electrons flowing in each CMD are multiplied) $n = M \times (4.1 \times 10^9) \times \mu^2 \times \eta \times RA \times T$ [e/pixel/flame] where M [lux] denotes the illuminance of the imaging surface of the CCD, $\mu$ denotes the size of each pixel location, $\eta$ denotes a quantum efficiency, RA denotes a rate of hole area, and T denotes an exposure time.

A: CMD multiplication rate

D [e/pixel/s]: dark current occurring at each pixel location

R [eRMS]: a noise derived from reading (occurring in a detection amplifier)

K [mv/e]: charge-voltage conversion factor set in the detection amplifier

A: CMD multiplication rate $F^2$: CMD excess noise factor (2) Parameters Relevant to Components Other than CCD $\beta$ [×100%]: attenuation ratio of a signal propagated over the CCD cable 120

G: gain produced by the processor (G=voltage level of output of processor/voltage level of input thereof)

Ncv [mV]: total voltage level of a noise occurring along the CCD cable 120 and a noise occurring in the processor 103

(Signal to Which a Gain is Given)

FIG. 22 shows the relationship between an illuminance on the imaging surface of a CCD and a signal-to-noise ratio which is established with the CMD multiplication rate set to 1, 3, and 10. The illuminance and signal-to-noise ratio are calculated by assigning parameter values to the formulae (1-2) and (2). FIG. 23 shows the relationship between the illuminance of the imaging surface of the CCD and an output voltage level. In FIG. 22, the signal-to-noise ratio (axis of ordinates) is calculated as S/N=20×log {formula (1-2)} (unit: dB).

(Advantages)

When the special light mode (observation under special light) is designated, an object from which feeble light is returned and which cannot be visualized by a typical CCD can be visualized owing to multiplication of electrons flowing in each CMD in the CCD and automatic gain control. Moreover, the signal-to-noise ratio relative to an image signal and the output voltage level of the image signal are improved. This results in a view image of excellent image quality (high signal-to-noise ratio) and proper brightness.

Information read from the ROM 170 may represent a type of endoscope or the brightness of an image displayed on the monitor 105 (output voltage level provided by the processor 103) instead of the CMD multiplication rates for CCD 109 predefined for the ordinary light mode and special light mode. Otherwise, correction data for a difference in the CCD multiplication rate for the CCD 109 from one pixel location to another may be transmitted to the processor 103.

Figure 30:
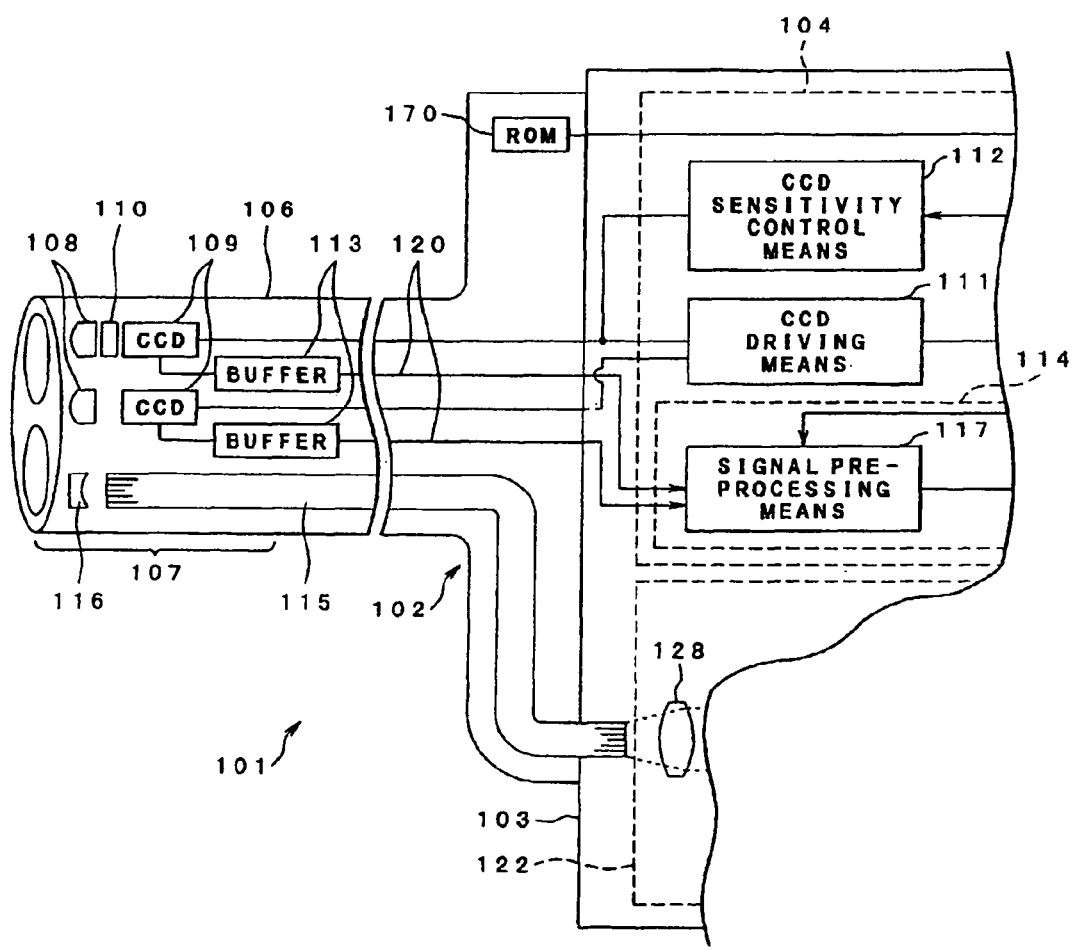
FIG. 30 is a block diagram showing a configuration of an endoscope system including two CCDs incorporated in the distal part of the endoscope.

As shown in FIG. 30, two CCDs may be incorporated in the distal part of an endoscope, and the first CCD of the CCDs may be used exclusively for the ordinary light mode (observation under ordinary light) and the second CCD thereof may be used exclusively for the special light mode (observation under special light). In this case, the CCD 109 employed in the present example is used as the second CCD. The first CCD dedicated to the ordinary light mode may be realized with the CCD 109 or the typical CCD.

The rotary filter 129 includes three filters associated with the special light mode. The number of filters associated with the special light mode need not be 3 but may be two or less or four or more.

The filters of the rotary filter 129 associated with the special light mode have the property of transmitting light whose wavelengths range from the ultraviolet spectrum to the blue spectrum. Alternatively, the filters may transmit light of wavelengths falling within the ultraviolet or blue spectrum alone. The filters may be used to perform auto-fluorescence imaging.

The spectrum of light transmitted by the filters of the rotary filter 129 associated with the special light mode ranges from the ultraviolet spectrum to the blue spectrum. The filters may transmit light of wavelengths falling within the visible spectrum. In this case, a drug (such as HpD, porphyrins, NPe6, ALA, m-THPC, ATX-S10, BPD-MA, ZnPC, SnET2, etc.) may be administered in order to perform drug fluorescence imaging for the purpose of photodynamic diagnosis.

The spectrum of light transmitted by the filters of the rotary filter 129 associated with the special light mode ranges from the ultraviolet spectrum to the blue spectrum. The filters may transmit light of wavelengths falling within the near-infrared spectrum. In this case, a drug (for example, indocyanine green that is a derivative marker antibody) may be administered in order to perform drug fluorescence imaging.

The spectrum of light transmitted by the filters of the rotary filter 129 associated with the special light mode ranges from the ultraviolet spectrum to the blue spectrum. The filters may transmit light of wavelengths ranging from the visible spectrum to the near-infrared spectrum. An image signal may be-picked up from the reflected light of the light. In this case, the filter 110 need not be included.

The mode switching means 135 is included in the processor 103 but may be included in the endoscope 102.

The processor 103 has the signal processing unit 104 and field-sequential light source unit 122 integrated thereinto. Alternatively, the signal processing unit 104 and field-sequential light source unit 122 may be provided as stand-alone apparatuses.

EXAMPLE 8

In Example 8, automatic light adjustment and automatic gain control are carried out for observation under ordinary light. For observation under special light, the CMD multiplication rate is manually set to a fixed value, automatic gain control is extended to a processor, an exposure time is made long, and light is emitted fully.

In Example 7, the exposure time is the same between the ordinary light mode (observation under ordinary light) and special light mode (observation under special light).

In Example 8, the exposure time is longer in the special light mode than in the ordinary light mode. Moreover, a high signal-to-noise ratio and a high output voltage level are attained.

(Constituent Features)

Figure 24:
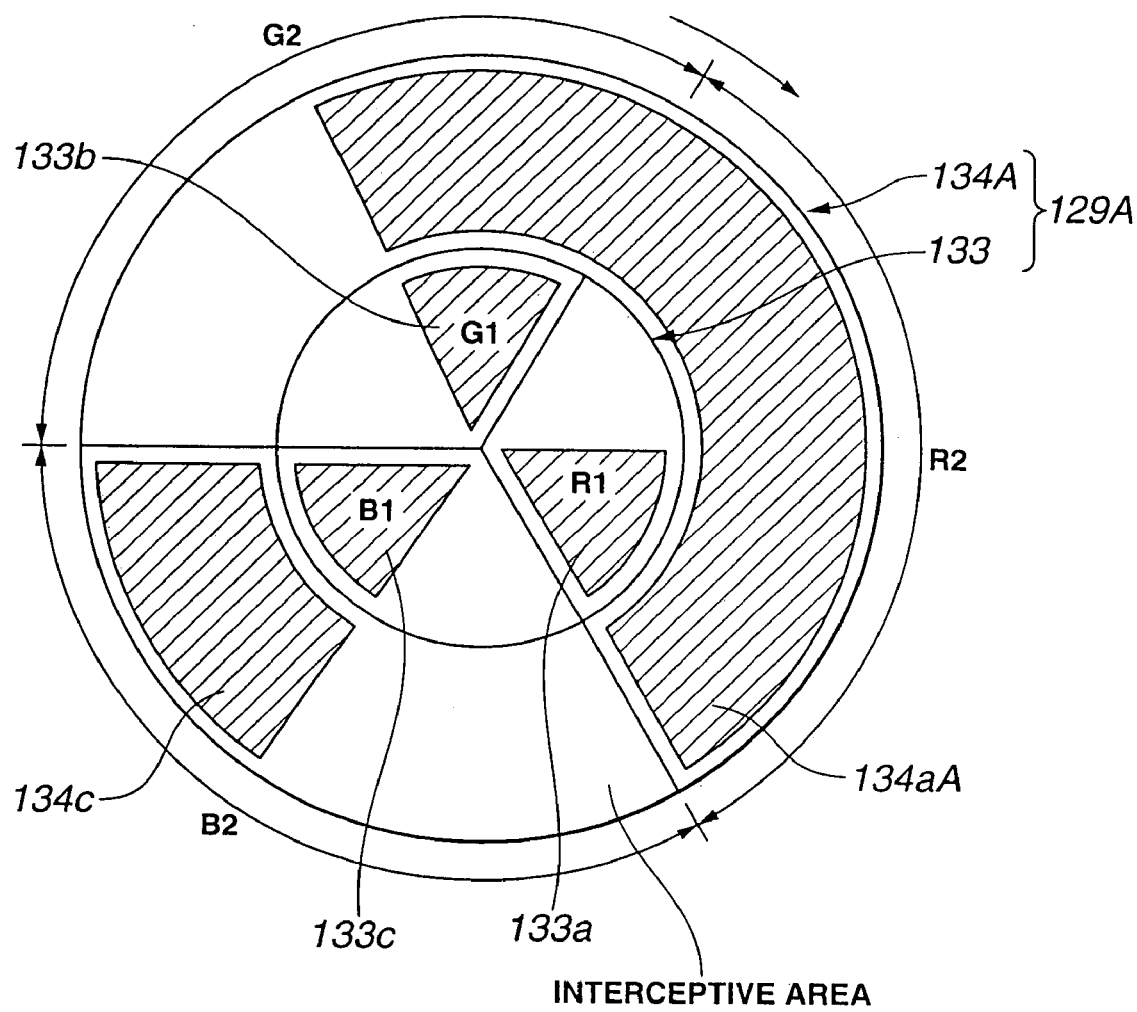
FIG. 24 to FIG. 27 are concerned with Example 8 of the present invention.
Figure 25:
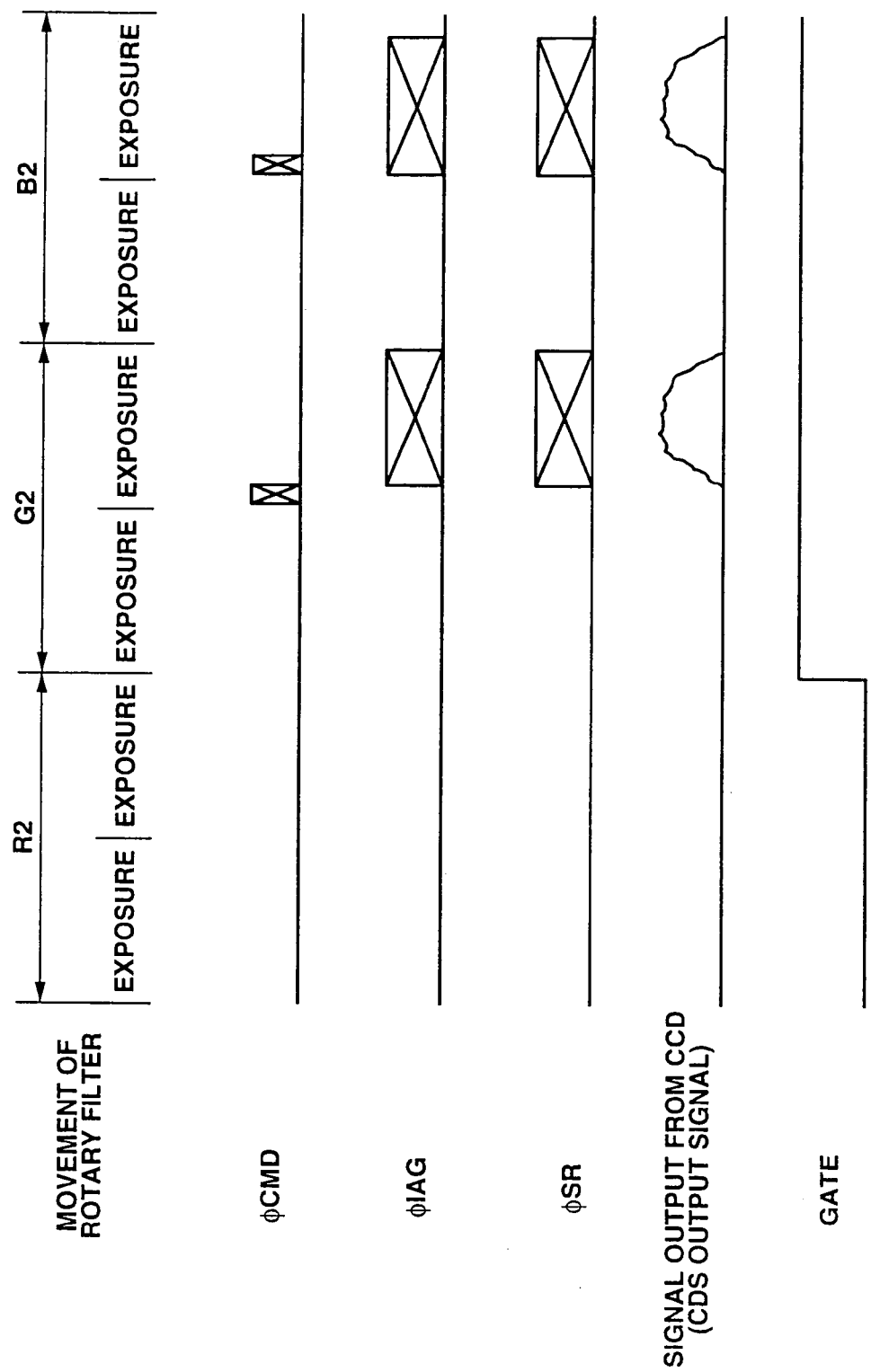
Figure 26:
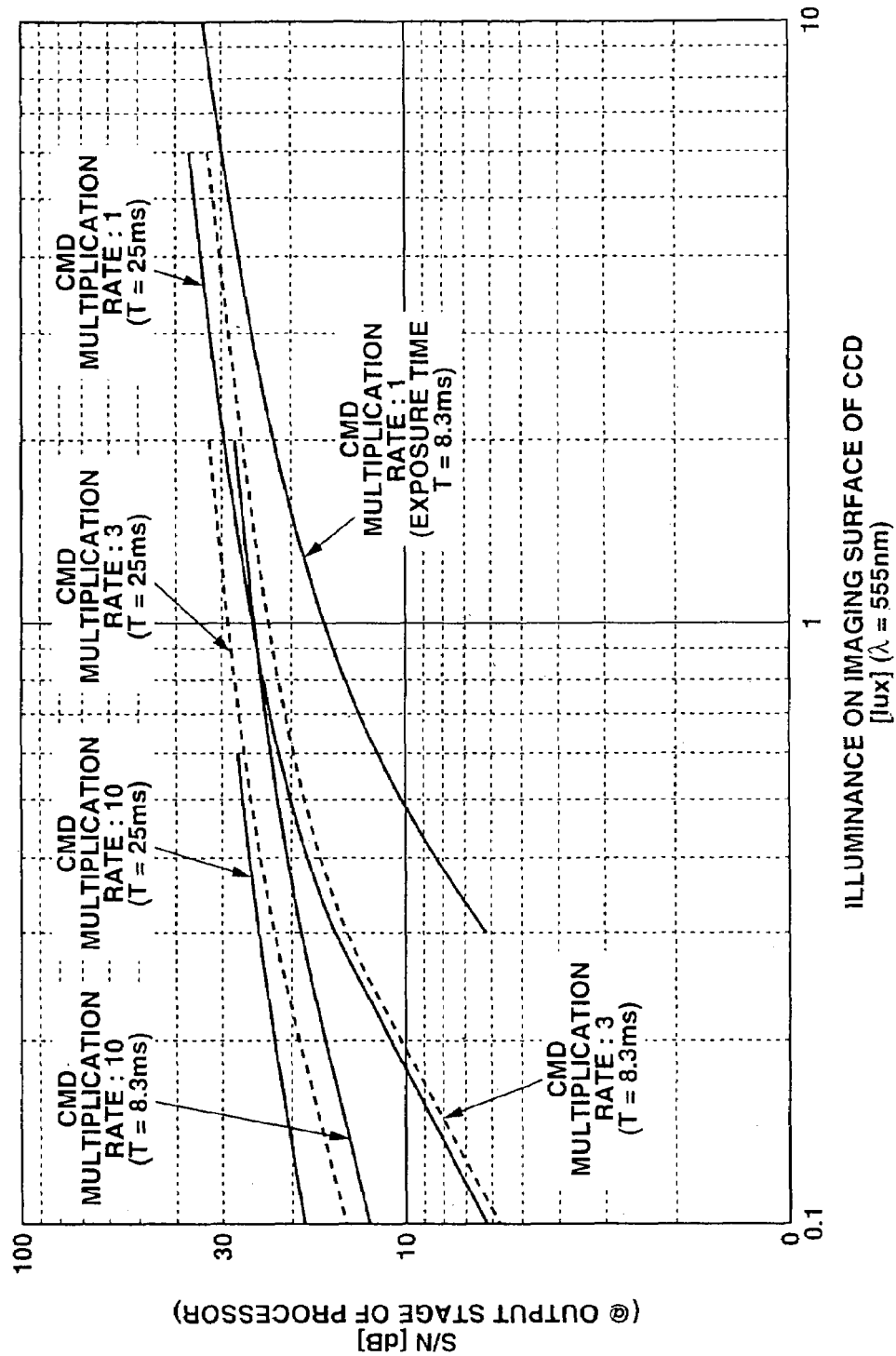
Figure 27:
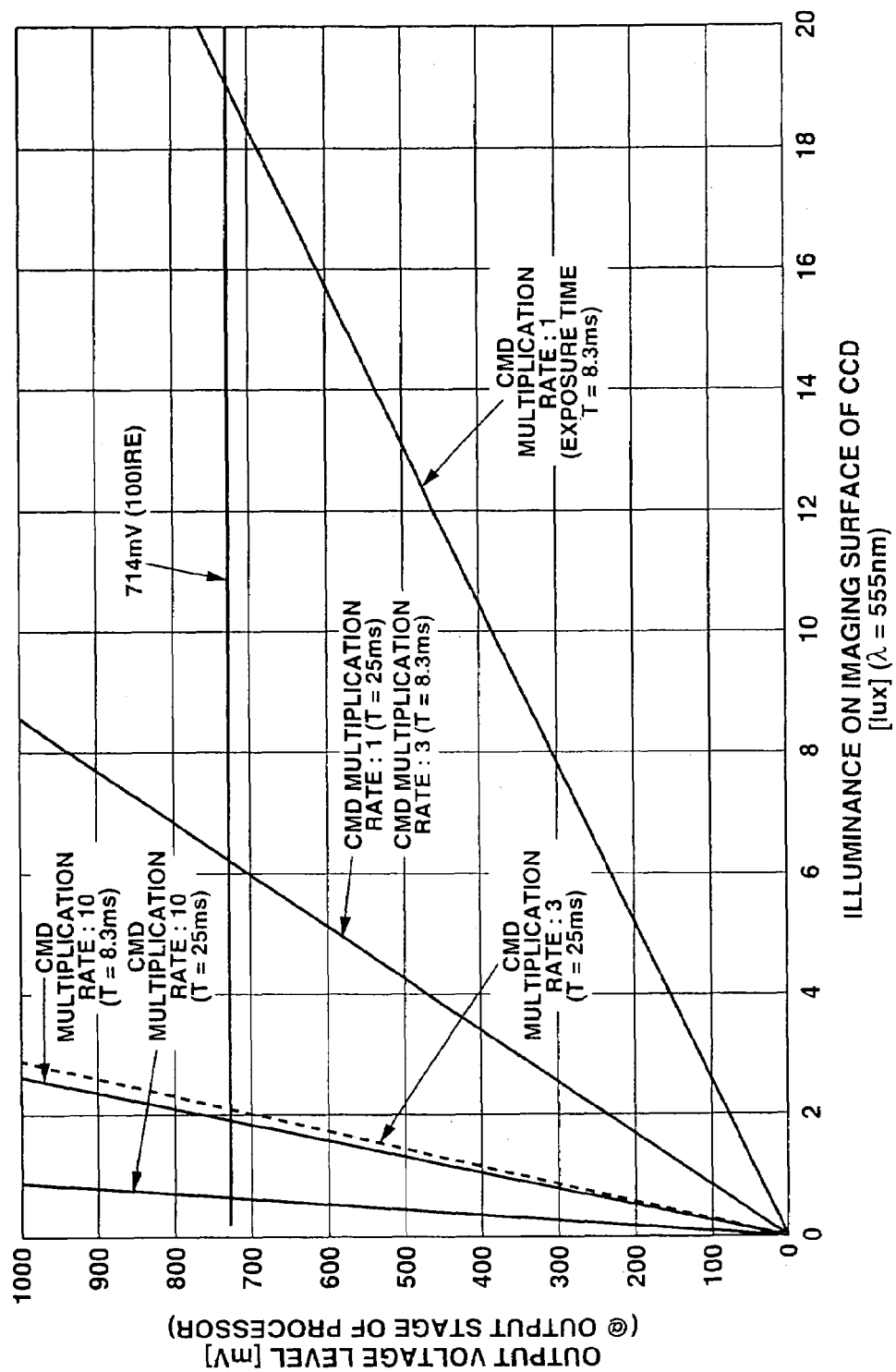

FIG. 24 shows the structure of a rotary filter. FIG. 25 is a timing chart showing the timings of signals used to drive a CCD in the special light mode. FIG. 26 is a graph indicating the relationship between the luminance on the imaging surface of the CCD and a signal-to-noise ratio (long exposure). FIG. 27 is a graph indicating the relationship between the luminance on the imaging surface of the CCD and an output voltage level (long exposure).

The description of a rotary filter 129A and other components identical to those of Example 7 will be omitted.

The rotary filter 129A consists, as shown in FIG. 24, of two filter sets, that is, filter sets 133 and 134A serving as inner and outer circumferential parts of the rotary filter 129A. The inner circumferential first filter set 133 consists of three filters 133a, 133b, and 133c used for the ordinary light mode (observation under ordinary light) as they do in Example 7. The outer circumferential second filter set 134A consists of two filters 134aA and 134c used for the special light mode (observation under special light). The filter sets 133 and 134A have spectral transmission properties thereof matched with respective purposes of observation.

In the present example, a filter for passing excitation light used to cause auto-fluorescence (light of wavelengths ranging from the ultraviolet spectrum to the blue spectrum) is adopted as the filter 134aA. The filter 134c is blocked. The second filter set 134A of the rotary filter 129A is divided into three areas R2, G2, and B2 as shown in FIG. 24. The filter 134aA occupies the whole area R2 and a half of the area G2. The filter 134c occupies nearly a half of the area B2 and is shaped like a sector. The filter 134aA and filter 134c are arranged circumferentially. The portion of the second filter set 134A other than the filters 134aA and 133c is blocked and determines an interception time (reading time) during which the CCD 109 is read. The control means 121 controls the CCD driving means 111 in response to a command output from the mode switching means 135 so that the CCD driving means will drive the CCD in line with a selected mode (ordinary light mode or special light mode).

FIG. 25 is a timing chart indicating the timings of signals used to drive the CCD in the special light mode. FIG. 25 indicates an exposure period and an interception period (reading period) determined by the second filter set (outer circumferential part) of the rotary filter 129A. Moreover, FIG. 25 indicates the relationship among a sensitivity control pulse φCMD, a vertical transfer pulse φIAG, and a horizontal transfer pulse φSR that are applied to the CCD 109, and an output signal of the CCD. The magnitudes of turns R2, G2, and B3 made by the rotary filter correspond to the sizes of the areas R2, G2, and B2 of the rotary filter 129A. The sensitivity control pulse φCMD, vertical transfer pulse φIAG, and horizontal transfer pulse φSR are output from the CCD sensitivity means 112 and CCD driving means 111 respectively during the interception period (reading period) succeeding the exposure period only when a gate pulse assumes an on voltage level. The CCD 109 provides the output signal during the interception period.

In Example 8, the gate pulse assumes the on voltage level only when the rotary filter 129A makes the turns G2 and B2. When the rotary filter 129A makes the turn R2, the gate pulse assumes an off voltage level. The CCD 109 does not provide the output signal. An exposure time is therefore equal to the sum of a period determined with the area R2 and a period determined with an exposure area of the area G2. The exposure time is therefore as long as nearly the triple of the one in Example 7. An image signal read from the CCD 109 during a period determined with an interceptive area of the area G2 is fed to the image memories included in the synchronizing means 163a and 163b. An image signal read from the CCD 109 during a period determined with an interceptive area of the area B2 is fed to the image memory included in the synchronizing means 163c. Incidentally, the gate pulse assumes the on voltage level in the ordinary light mode. After an object is exposed to light passing through the first filter set composed of the filters 133a, 133b, and 133c, the CCD 109 is read.

(Operations)

Operations exerted in the special light mode will be described below. Operations exerted in the ordinary light mode are identical to those in Example 7.

Excitation light (of wavelengths ranging from the ultraviolet spectrum to the blue spectrum in the present example) emitted from the lamp 127 passes through the second filter set 134A. According to the present example, only the excitation light passing through the filter 134aA is intermittently irradiated to a living tissue. In the present example, no light passes through the filter 134c and is irradiated to the living tissue. An exposure time during which light passing through the filter 134aA is irradiated is generally three times longer than that in Example 7. Charge carriers are received and accumulated in the CCD 109 during a period during which excitation light passing through the filter 134aA of the second filter set is irradiated to the living tissue. The charge carriers are read during an interception period (reading period) determined with the interceptive area of the area G2. An image signal output from the CCD is fed to the signal processing means 114. The signal processing means 114 processes the signal read during the period determined with the interceptive area of the area G2. Consequently, a view image produced with special light is displayed on the monitor 105.

Now, a description will be made of a signal-to-noise ratio relative to a signal representing the view image displayed on the monitor 105 (image produced with light stemming from auto-fluorescence in the present example) and the brightness of the view image. The signal-to-noise ratio and brightness are attained with an exposure time extended and the CMD multiplication rate for the CCD 109 raised.

In Example 8, an exposure time T' shall be approximately three times longer than the exposure time T in Example 1. Moreover, the CMD multiplication rate for the CCD 109 shall be set to 3 and 10. FIG. 26 and FIG. 27 graphically show the relationship between the illuminance on the imaging surface of the CCD and the signal-to-noise ratio or the output voltage level which is established under the above conditions.

As seen from FIG. 26 and FIG. 27, when a living tissue is exposed for a longer exposure time (irradiation time) with the CMD multiplication rate for the CCD 109 held constant, the signal-to-noise ratio and output voltage level get higher. When the CMD multiplication rate is raised and the exposure time is extended, the signal-to-noise ratio and output voltage level get higher.

(Advantages)

In the special light mode (observation under special light), even if light returning from an object is too feeble to visualize the object using a typical CCD, the object can be visualized owing to multiplication of electrons flowing in each CMD in the CCD, extension of an exposure time, and automatic gain control. Moreover, a signal-to-noise ratio and an output voltage level are raised. Consequently, a view image of excellent image quality (high signal-to-noise ratio) and proper brightness can be produced.

Information read from the ROM 170 may represent a type of endoscope or the brightness of an image displayed on the monitor 105 (output voltage level of processor 103) instead of the CMD multiplication rate for the CCD 109 defined for the ordinary light mode or special light mode. Otherwise, correction data for a difference in the CMD multiplication rate for the CCD 109 from one pixel location to another may be transmitted to the processor 103.

Two CCDs may be incorporated in the distal part of an endoscope. The first CCD of the two CCDs may be used exclusively for the ordinary light mode (observation under ordinary light), and the second CCD thereof may be used exclusively for the special light mode (observation under special light). In this case, the CCD 109 employed in the present example is adopted as the second CCD. The first CCD dedicated to the ordinary light mode may be realized with the CCD 109 or a typical CCD.

In the present example, reading of the CCD is performed twice during one full turn of the rotary filter. The gate pulse may be applied only once while the rotary filter makes the turns R2, G2, and B2. In this case, the exposure time set in Example 1 can be extended to be five times longer at most. Two filters included in the rotary filter 129A are associated with the special light mode. The number of filters associated with the special light mode need not be confined to two but may be one.

The filters of the rotary filter 129A associated with the special light mode have the property of transmitting light whose wavelengths range from the ultraviolet spectrum to the blue spectrum. Alternatively, filters for transmitting light whose wavelengths fall within the ultraviolet or blue spectrum alone may be employed for auto-fluorescence imaging.

The filters of the rotary filter 129A associated with the special light mode have the spectral property of transmitting light whose wavelengths range from the ultraviolet spectrum to the blue spectrum. Alternatively, the filters may transmit light of wavelengths falling within the visible spectrum. In this case, a drug (HpD, porphyrins, NPe6, ALA, m-THPC, ATX-S10, BPD-MA, ZnPC, SnET2) is administered in order to perform drug fluorescence imaging for the purpose of photodynamic diagnosis.

The filters of the rotary filter 129A associated with the special light mode have the spectral property of transmitting light whose wavelengths range from the ultraviolet spectrum to the blue spectrum. Alternatively, the filters may transmit light of wavelengths falling within the near-infrared spectrum. In this case, a drug (for example, indocyanine green that is a derivative marking antibody) is administered in order to perform drug fluorescence imaging.

The filters of the rotary filter 129A associated with the special light mode have the spectral property of transmitting light whose wavelengths range from the ultraviolet spectrum to the blue spectrum. Alternatively, the filters may transmit light of wavelengths ranging from the visible spectrum to the near-infrared spectrum. An image signal may then be picked up from the reflected light of the light. In this case, the filter 110 need not be included.

The mode switching means 135 is included in the processor 103, but may be included in the endoscope 102.

The processor 103 has the signal processing unit 104 and field-sequential light source unit 122 integrated thereinto. The signal processing unit 104 and field-sequential light source unit 122 may be included as stand-alone apparatuses.

EXAMPLE 9

Example 9 is such that the CMD multiplication rate is varied automatically depending on whichever of observation under ordinary light and observation under special light is designated.

In Example 7, the CMD multiplication rate for the CCD is set to a fixed value. The CMD multiplication rate is adjusted manually. For optimizing the brightness of an image displayed on the monitor, the output signal of the CCD is electrically amplified and thus adjusted through automatic gain control.

(Constituent Features)

Figure 28:
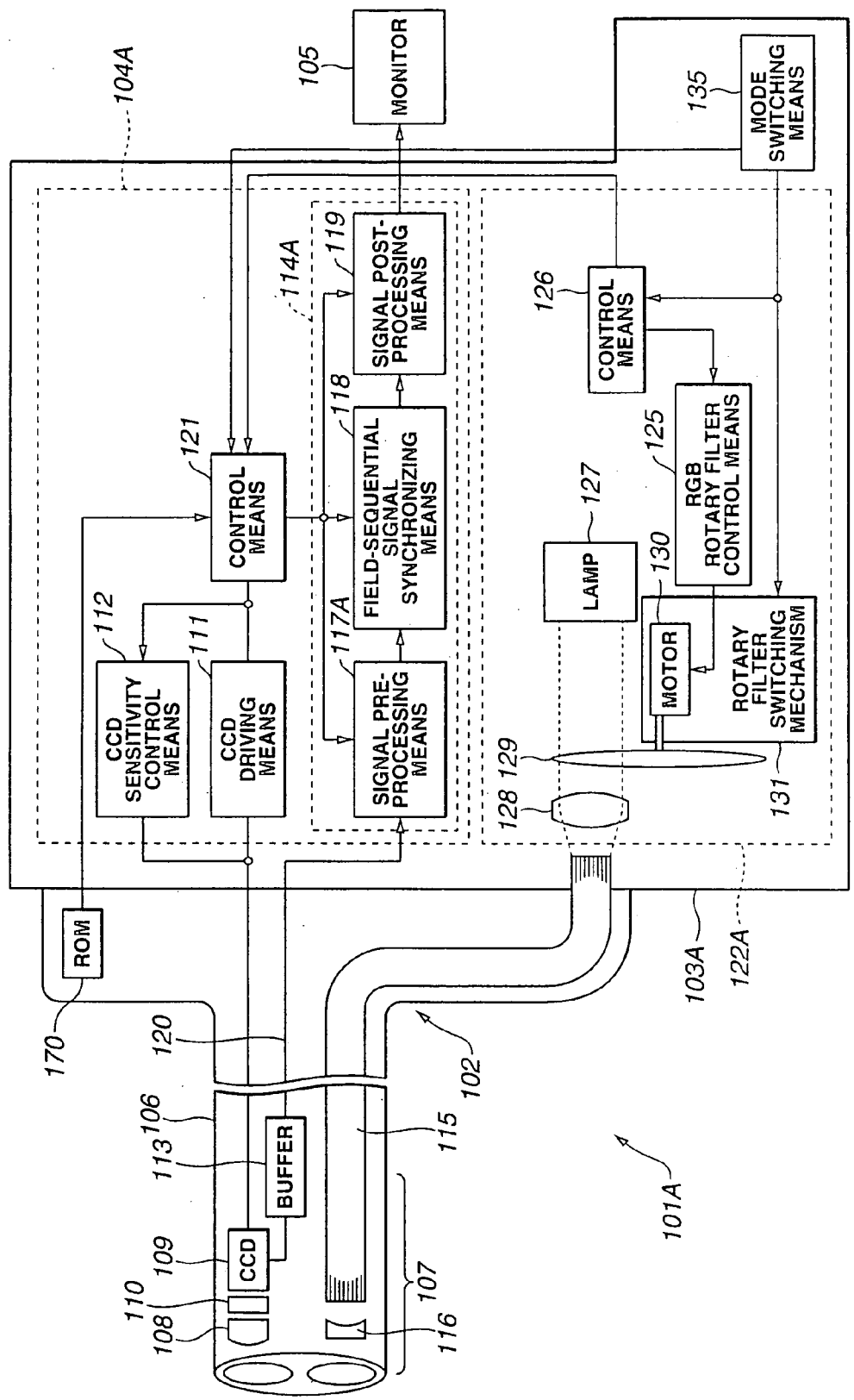
FIG. 28 and FIG. 29 are concerned with Example 9 of the present invention.
Figure 29:
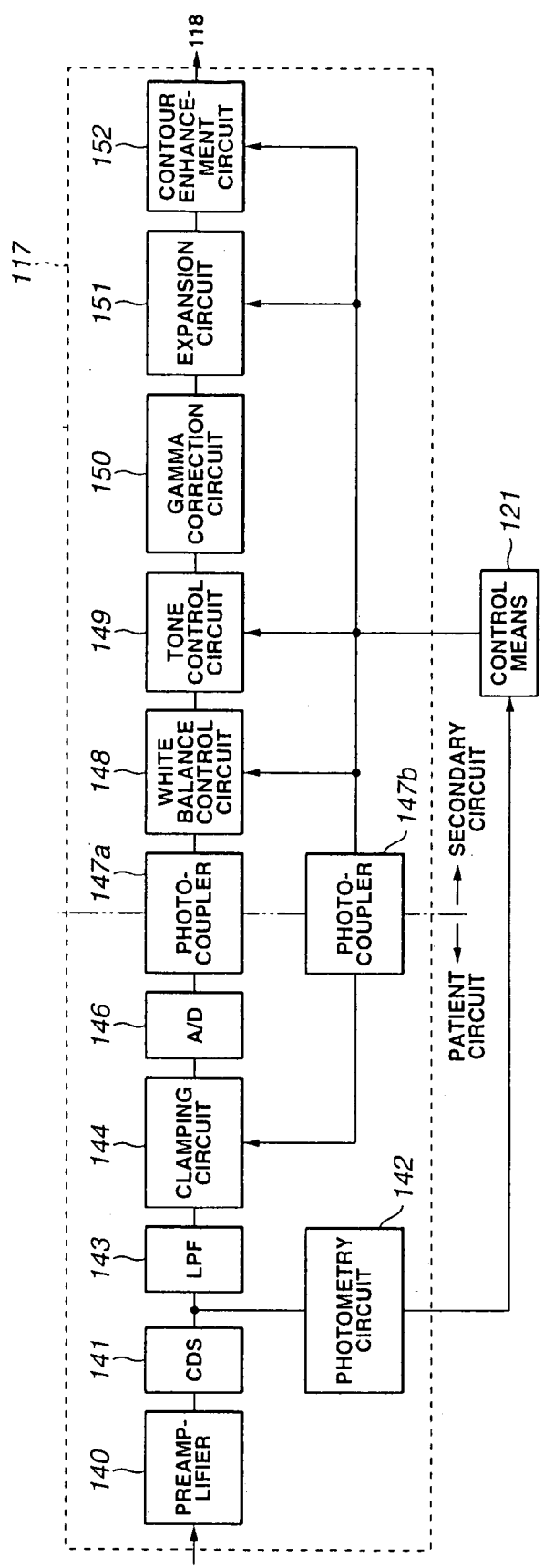

FIG. 28 is a block diagram schematically showing the configuration of an endoscope system. FIG. 29 is a block diagram showing a signal pre-processing means included in a signal processing means.

The description of components identical to those shown in FIG. 17 will be omitted.

The automatic gain control circuit 145, iris diaphragm 123, and diaphragm control means 124 included in Example 7 are excluded in Example 9.

The photometry means 142 calculates an average of voltage levels assumed by the output signal of the CCD 109 during one field, and outputs the average to the CCD sensitivity control means 112 via the control means 121. The CCD sensitivity control means 112 calculates the number of applications of a pulse per unit time associated with a CMD multiplication rate that permits the output signal of the CCD 109 to assume a set voltage level. Consequently, the pulse is applied to the CCD 109 by the calculated number of times during an interception period (reading period) during which the CCD 109 is read.

(Operations)

A user manipulates, for example, a mode selection switch included in the mode switching means 135 so as to select a desired mode (ordinary light mode or special light mode). In the field-sequential light source unit 122A, the rotary filter switching mechanism 131 turns the rotary filter 129 according to the selected mode. Illumination light matched with the selected mode is routed to the rear end of the light guide 115 via the rotary filter 129, and irradiated to a living tissue. Since the field-sequential light source unit 122a has no diaphragm, the intensity of illumination light emitted from the distal end of the endoscope 102 remains constant.

Field-sequential light rays (of red, blue, and green) are reflected from a living tissue in the ordinary light mode, while special light such as light stems from fluorescence exhibited by the living tissue in the special light mode. The reflected light rays or light stemming from fluorescence is projected on the CCD 109 in order to pick up an image signal. A resultant video signal is fed to the signal processing means 114A. The signal processing means 114A processes the output signal of the CCD 109. Consequently, a view image is displayed on the monitor 105.

When an object (living tissue) exhibiting certain brightness is imaged using the CCD 109, a signal-to-noise ratio (FIG. 22) and an output voltage level (FIG. 23) vary depending on the CMD multiplication rate for the CCD 109. The photometry means 142 calculates an average of voltage levels assumed by the output signal of the CCD 109 during one field, and outputs the average to the CCD sensitivity control means 112 via the control means 121. The CCD sensitivity control means 112 calculates the number of applications of a pulse per unit time associated with a CMD multiplication rate for the CCD 109 that permits the output signal of the CCD 109 to assume a voltage level and represent an image of brightness of a user-designated level to be displayed on the monitor 105. The CCD sensitivity control means 112 outputs the number of applications of the pulse per unit time to the CCD 109. Specifically, when the voltage level of a signal output from the processor 103A is lower than a set value, the CMD multiplication rate for the CCD 109 is automatically raised. When the voltage level of a signal output from the processor 103A is higher than the set value, the CMD multiplication rate for the CCD 109 is automatically lowered. A user can always view an image of brightness of any user-designated level on the monitor 105.

Moreover, when light returning from an object is especially feeble, the CMD multiplication rate for the CCD 109 is automatically raised. For example, as seen from FIG. 22, when the CMD multiplication ratio is set to a large value, a signal-to-noise ratio is higher than it is when the CMD multiplication rate is set to a small value. An excellent view image can therefore be produced.

A signal output from the output stage of the processor 103A is amplified by raising the CMD multiplication ratio for the CCD 109. Compared with when the signal output from the CCD 109 is electrically amplified, influence of a noise can be suppressed. This results in an image benefiting from a high signal-to-noise ratio.

(Advantages)

The CMD multiplication ratio for a CCD is automatically controlled based on the brightness of an object. This results in a view image of excellent image quality (high signal-to-noise ratio) and proper brightness. Moreover, the configuration of a light source unit can be simplified.

An appendix and variant of the present example are identical to those of Example 7.

In the present example, the CMD multiplication rate for the CCD 109 is varied between the ordinary light mode and special light mode in order to make the brightness of an image displayed on the monitor 105 constant. Alternatively, in the ordinary light mode, similarly to that in Example 1, the iris diaphragm included in the light source unit may be controlled to vary the intensity of light to be irradiated to a living tissue.

EXAMPLE 10

The present example is such that the CMD multiplication ratio is automatically varied depending on whichever of observation under ordinary light and observation under special light is designated. For the observation under special light, an object is exposed to light for a long period of time.

In Example 9, an exposure time is the same between the ordinary light mode (observation under ordinary light) and special light mode (observation under special light).

In contrast, in Example 10, an exposure time for the special light mode is longer than that for the ordinary light mode. Thus, the present example attempts to attain a higher signal-to-noise ratio than that attained in Example 9.

A rotary filter (second filter set) is structured as shown in FIG. 24. The timings of signals applied in order to drive the CCD in the special light mode are defined as shown in FIG. 25.

(Constituent Features)

The description of components identical to those of Example 9 will be omitted.

Differences of Example 19 from Example 9 lie in the structure of a rotary filter 129A and the timings of signals applied to drive a CCD in the special light mode.

(Operations)

Operations to be exerted in the special light mode will be described below. Operations to be exerted in the ordinary light mode are identical to those in Example 9.

Excitation light emitted from the lamp 127 (light of wavelengths ranging from the ultraviolet spectrum to the blue spectrum) passes through the second filter set 134A. In the present example, the excitation light passing through the filter 134aA is intermittently irradiated to a living tissue. An irradiation (exposure) time is approximately three times longer than that in Example 9. No light passes through the filter 134c and is irradiated in the present example. The CCD 109 receives light stemming from fluorescence exhibited by the living tissue to which the excitation light is irradiated. Accumulated charge carriers are read from the CCD 109 during an interception period (reading period) determined with the interceptive area of the area G2. An acquired imaging signal is fed to the signal processing means 114A. The signal processing means 114A processes the signal. Consequently, a view image produced with special light is displayed on the monitor 105.

Now, a description will be made of a signal-to-noise ratio relative to a signal representing a view image displayed on the monitor 105 (an image produced with auto-fluorescence in the present example) and the brightness of the view image. The signal-to-noise ratio and brightness are attained with an exposure time extended and the CMD multiplication ratio for the CCD 109 raised.

In Example 10, an exposure time T' is approximately three times longer than the exposure time T in Example 9. Moreover, the CMD multiplication rate for the CCD 109 is set to 3 and 10. FIG. 26 and FIG. 27 graphically show the relationship between the illuminance on the imaging surface of the CCD and a signal-to-noise ratio or an output voltage level which is established under the above conditions.

Assume that an object (living tissue) of certain brightness is imaged using the CCD 109 with an exposure time extended. A signal-to-noise ratio (FIG. 26) and output voltage level (FIG. 27) vary depending on the CMD multiplication rate for the CCD 109. With the CMD multiplication rate held unchanged, the longer the exposure time is, the higher the signal-to-noise ratio and output voltage level are. Namely, the signal-to-noise ratio and output voltage level attained in the present example are higher than those attained in Example 9. The photometry means 142 calculates an average of voltage levels assumed by an output signal of the CCD 109 during one field, and outputs the average to the CCD sensitivity control means 112 via the control means 121. The CCD sensitivity control means 112 calculates the number of applications of a pulse per unit time associated with the CMD multiplication rate for the CCD 109 that permits the output signal to represent an image of brightness of a certain user-designated level. The CCD sensitivity control means 112 outputs the number of applications of the pulse per unit time to the CCD 109. Specifically, when the output voltage level provided by the processor 103A is lower than a set value, the CMD multiplication rate for the CCD 109 is automatically raised. When the output voltage level is higher than the set value, the CMD multiplication rate for the CCD 109 is automatically lowered. Consequently, a view image of brightness of the user-designated level can always be viewed on the monitor.

Moreover, when light returning from an object is feeble, the CMD multiplication rate for the CCD 109 is automatically raised. As seen from FIG. 26, when the CMD multiplication rate is set to a larger value, if an exposure time is extended, a signal-to-noise ratio is much higher than it is when the CMD multiplication rate is set to a small value.

A signal output from the output stage of the processor 103A is amplified by raising the CMD multiplication rate for the CCD 109. Compared with when the output signal of the CCD 109 is electrically amplified, influence of a noise is limited. This results in an image benefiting from a high signal-to-noise ratio.

(Advantages)

When the special light mode (observation under special light) is designated, the CMD multiplication rate for the CCD is automatically controlled based on the intensity of the feeble light. Consequently, a view image of excellent image quality (high signal-to-noise ratio) and proper brightness can be produced. Moreover, when an exposure time is extended, a view image will benefit from a higher signal-to-noise ratio. Moreover, the structure of the light source unit can be simplified.

An appendix and variant of the present example are identical to those of Example 8.

In the present example, the CMD multiplication rate for the CCD 109 is controlled in order to make the brightness of an image on the monitor 105 constant depending on whichever of the ordinary light mode or special light mode is designated. When the ordinary light mode is designated, similarly to Example 1, the iris diaphragm included in the light source unit may be controlled in order to vary the intensity of light to be irradiated to a living tissue.

Examples composed of parts of the constituent features of the aforesaid examples also belong to the present invention.

INDUSTRIAL APPLICABILITY

As described so far, according to the present invention, a view image of proper brightness can be produced irrespective of the type of endoscope. Moreover, a means for controlling the sensitivity of a solid-state imaging device can freely control the sensitivity by adjusting the amplitude of a sensitivity control pulse and the number of applications thereof per unit time. Owing to the sensitivity control, a high-sensitivity solid-state imaging device can be realized without a noise derived from multiplication of electrons and without the necessity of cooling. Consequently, an endoscope offering excellent image quality and capable of being inserted smoothly can be realized. Moreover, the sensitivity control means can set the sensitivity of the solid-state imaging device according to a type of endoscope or the property of each solid-state imaging device. Eventually, a view image of proper brightness can be produced irrespective of the type of endoscope or the property of each solid-state imaging device.

The invention claimed is:

1. An endoscope system comprising:

an endoscope having one or more solid-state imaging devices, each solid-state imaging device comprising a charge multiplication mechanism for varying a sensitivity by varying a charge multiplication rate in accordance with the number of pulses or amplitude of the pulses provided to the one or more solid-state imaging devices;

a signal processing unit for processing an output signal from the one or more solid-state imaging devices;

a light source unit for selectively irradiating first light to perform ordinary light observation and second light to perform special light observation to an object;

an observation mode switching device for switching between the ordinary light observation by the first light and the special light observation by the second light; and a sensitivity control device for controlling the charge multiplication rate by varying the number of pulses or the amplitude of the pulses provided to the one or more solid-state imaging devices so that a level of the output signal from the one or more solid-state imaging devices may be a predetermined level; and, an automatic gain control circuit for amplifying an output signal from the one or more solid-state imaging devices so that the level of the output signal becomes said predetermined level when the level of the output signal is less than said predetermined level, wherein the sensitivity control device varies the charge multiplication rate of the one or more solid-state imaging devices depending upon whether the first light is irradiated to the object or the second light is irradiated to the object.

2. An endoscope system according to claim 1, further comprising an irradiating light switching device for switching the light irradiated to the object between the first light and the second light in accordance with an output from the observation mode switching device.

3. An endoscope system according to claim 2, wherein the sensitivity control device varies the charge multiplication rate of the one or more solid-state imaging devices in accordance with a signal from the observation mode switching device.

4. An endoscope system according to claim 2, wherein the charge multiplication mechanism is provided for each pixel or at a preceding stage of a detection amplifier.

5. An endoscope system according to claim 2, wherein the charge multiplication mechanism is provided at a preceding stage of a detection amplifier.

6. An endoscope system according to claim 2, wherein the one or more solid-state imaging devices detects an object image by the first light and an object image by the second light.

7. An endoscope system according to claim 6, wherein the effective period during which charges are accumulated in the one or more solid-state imaging devices when the first light is irradiated to the object is different from that when the second light is irradiated to the object.

8. An endoscope system according to claim 2, wherein the one or more solid-state imaging devices comprises a first solid-state imaging device for detecting the object image by the second light and a second solid-state imaging device for detecting the object image by the first light.

9. An endoscope system according to claim 2, wherein the second light is of wavelength falling within a wavelength band of excitation light to perform observation under fluorescent light.

10. An endoscope system according to claim 9, wherein the one or more solid-state imaging devices detects an object image by the first light and an object image by the second light.

11. An endoscope system according to claim 10, wherein the effective period during which charges are accumulated in the one or more solid-state imaging devices when the second light is irradiated to the object is longer than that when the first light is irradiated to the object.

12. An endoscope system according to claim 9, wherein the one or more solid-state imaging devices comprises a first solid-state imaging device for detecting the object image by the second light and a second solid-state imaging device for detecting the object image by the first light.

13. An endoscope system according to claim 2, wherein the sensitivity control device controls the number of the pulses or the amplitude of the pulses provided to the one or more solid-state imaging devices so that the charge multiplication rate may be a predetermined value.

14. An endoscope system according to claim 13, further comprising a manual input device for setting the charge multiplication rate.

15. An endoscope system according to claim 13, wherein the signal processing unit comprises an automatic gain control circuit for amplifying an output signal from the one or more solid-state imaging devices when the level of the output signal is less than a predetermined level.

16. An endoscope system according to claim 15, wherein the automatic gain control circuit amplifies the output signal from the one or more solid-state imaging devices when the level of the output signal supplied to a monitor is less than a predetermined level.

17. An endoscope system according to claim 2, wherein the light source unit includes a lamp and a filter unit provided in the optical path between the object and the lamp and comprises a first filter to transmit light from the lamp so as to irradiate the first light to the object and a second filter to transmit light from the lamp so as to irradiate the second light to the object, and the irradiating light switching device comprises a filter switching device for switching the filter unit provided in the optical path between the first filter and the second filter.

18. An endoscope system according to claim 17, wherein the filter unit is provided with a rotary filter rotated by a motor, and the time that the second light is irradiated to the object via the second filter is longer than the time that the first light is irradiated to the object via the first filter.

19. An endoscope system according to claim 18, further comprising;
an iris diaphragm which adjusts light level of the light irradiated to the object; and
an iris diaphragm controller;
wherein the iris diaphragm controller controls the iris diaphragm such that the iris diaphragm is opened when the light irradiated to the object is switched by the filter switching device from the first light to the second light.

20. An endoscope system according to claim 17, wherein the first filter is provided along the periphery of the of the rotary filter, and the second filter is provided along the periphery of the rotary filter substantially in parallel to the first filter.

21. An endoscope system according to claim 2, wherein the sensitivity control device controls the number of the pulses or the amplitude of the pulses provided to the one or more solid-state imaging devices when the level of the output signal supplied to a monitor is less than a predetermined level.

22. An endoscope system according to claim 21, wherein the sensitivity control device controls the number of the pulses or the amplitude of the pulses provided to the one or more solid-state imaging devices depending on the brightness of the object.

* * * * *

UNITED STATES PATENT AND TRADEMARK OFFICE
CERTIFICATE OF CORRECTION

| | |
|---|---|
| PATENT NO. | : 7,258,663 B2 |
| APPLICATION NO. | : 10/755559 |
| DATED | : August 21, 2007 |
| INVENTOR(S) | : Nobuyuki Doguchi et al. |

Page 1 of 1

It is certified that error appears in the above-identified patent and that said Letters Patent is hereby corrected as shown below:

<u>Title Page:   Item 30</u>

The Foreign Application Priority data was omitted should read

Foreign Application Priority Data

May 18, 1999      (JP)……………………..H11-137730

<u>Column 33, Claim 5, Line 20:</u>

"claim 2" should read -- claim 5 --

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,258,663 B2 |
| APPLICATION NO. | : 10/755559 |
| DATED | : August 21, 2007 |
| INVENTOR(S) | : Nobuyuki Doguchi et al. |

It is certified that error appears in the above-identified patent and that said Letters Patent is hereby corrected as shown below:

Title Page:

PCT Application information is not included should read as follow:

"This application is a CON of 09/743,994 01/017/2001 PAT 6,902,527

Which is a 371 of PCT/JP00/03132 05/16/2000"

Column 33, Claim 5, Line 20:

"claim 2" should read -- claim 4 --

Signed and Sealed this

Twenty-fifth Day of November, 2008

JON W. DUDAS
*Director of the United States Patent and Trademark Office*